United States Patent [19]

Mlodozeniec et al.

[11] 4,029,757

[45] June 14, 1977

[54] MANUFACTURE OF PHARMACEUTICAL UNIT DOSAGE FORMS

[75] Inventors: Arthur Roman Mlodozeniec, Montclair; Lawrence Samuel White, Ramsey, both of N.J.

[73] Assignee: Hoffmann-La Roche Inc., Nutley, N.J.

[22] Filed: Dec. 15, 1975

[21] Appl. No.: 640,652

[52] U.S. Cl. .................................. 424/27; 156/204; 156/227; 156/474; 424/16; 424/19; 424/21
[51] Int. Cl.² ...................... A61K 9/70; B32B 33/00
[58] Field of Search .................. 424/16, 19, 21, 27; 128/260; 156/204, 227

[56] References Cited

UNITED STATES PATENTS

| 2,836,291 | 5/1958 | Stroop | 424/21 |
| 3,007,848 | 11/1961 | Stroop | 424/16 |
| 3,917,251 | 11/1975 | DeLise et al. | 270/37 |
| 3,917,255 | 11/1975 | Watrous | 270/86 |

*Primary Examiner*—Dolph H. Torrence
*Attorney, Agent, or Firm*—Samuel L. Welt; Bernard S. Leon; R. Hain Swope

[57] ABSTRACT

Pharmaceutical dosage forms comprising an edible web having deposited thereon or at least partially thereon a particulate medicament, the webs being thereafter fabricated and finished to pharmaceutically elegant solid dosage forms having no medicament exposed on an exterior surface. The dosage forms have a consistency of release of medicament which can be controlled to exacting specifications. The disclosed solid dosage forms are prepared by high speed automated equipment and the process by which they are made is characterized by non-destructive quality control analysis and performance evaluation both conducted on-line and integrated into the manufacturing operation. Included in the scope of the disclosed invention are certain apparatus and methods of manufacture.

4 Claims, 12 Drawing Figures ial must be evaluated before use in terms of potential incompatibilities with the medicaments present. Further, certain of these materials, e.g. lubricants, may present problems concerning the bioavailability of the active ingredient. Also, the presence of such materials must be considered in analytical procedures utilized to test for potency etc. of the finished dosage form.

MANUFACTURE OF PHARMACEUTICAL UNIT DOSAGE FORMS

BACKGROUND OF THE INVENTION

The orally administered solid unit dosage forms heretofore recognized in the pharmaceutical industry are generally divisible into two basic forms, i.e., tablets and capsules. There are various broad categories of both tablets and capsules recognized in the art such as, for example, those which are enteric coated to release medication in the intestinal tract, those which, by various mechanisms, release medication over an extended period of time, effervescents and the like. By and large such conventional solid oral dosage forms suffer from a number of disadvantages.

First, conventional solid oral unit dosage forms are disadvantageous in that each contains, admixed with the active ingredient a plurality of various substances which are termed "therapeutically inert or non-toxic, pharmaceutical adjunct materials". Such materials fall under the art-recognized categories of diluents, excipients, binders, lubricants, disintegrants, stabilizers, buffers, preservatives and the like. Although these materials are recognized as indispensible in the art of pharmaceutical compounding, their use nonetheless presents problems which must be dealt with from a viewpoint of cost, final size and weight of the dosage unit and the like. Additionally, each such adjunct material must be evaluated before use in terms of potential incompatibilities with the medicaments present. Further, certain of these materials, e.g. lubricants, may present problems concerning the bioavailability of the active ingredient. Also, the presence of such materials must be considered in analytical procedures utilized to test for potency etc. of the finished dosage form.

A second primary disadvantage in solid oral unit dosage forms known to the art is that the methods available for assay thereof involve destruction of the dosage form thereby permitting the testing of only a small percentage of such forms actually produced. Therefore, it is recognized in the art that there can be considerable deviation within a given batch of such dosage forms since the mean of dosage, performance, etc. for each batch deviation is determined by analysis of a relatively minor number of samples.

The batch concept in itself is a disadvantage to prior art oral solid dosage forms simply from the viewpoint of the economics of the batch designation, control and evaluation.

In accordance with the present invention, solid dosage units primarily for oral ingestion are provided which are producible in large numbers at high speed and, because they are prepared by a method unique in the pharmaceutical industry, they do not suffer from the above enumerated disadvantages of currently available solid oral dosage forms, i.e., tablets and capsules. This method is highly advantageous in that it: eliminates the necessity for batch requirements as they are conventionally recognized; provides for continuous on-line analysis for potency as well as on-line performance evaluation of the dosage forms as they are being produced; provides the substantial elimination of the necessity of mixing conventional pharmaceutical adjunct materials with the medicaments with the exception of glidants which may be required to facilitate the flow of powders and/or certain other materials advantageous for product performance; and provides pharmaceutically elegant unit dosage forms which can be engineered to release medicament at any desired rate and which are capable of a rate of release faster than commercial tablets and capsules presently available. In summary, the dosage forms of the invention provide assurance that a larger percent of a more accurately measured amount of medication will be available in a more precisely controlled time after ingestion than is the case with present commercial units.

The oral unit dosage forms of the present invention are advantageous in a number of important respects, foremost of which is the fact that they are substantially qualified by on-line procedures during high-speed, substantially automated manufacturing operations. In addition, the dosage forms of the present invention are also advantageous in that the medicament contained therein is released for absorption with exceptional uniformity over a large number of dosage units. Further, the dosage units of the invention can be engineered to release medication within a shorter period of time after ingestion than is possible with solid oral dosage forms, e.g., tablets and capsules, presently available. Therefore, the dosage units of the invention provide superior consistency both in content of medicament and release thereof for absorption.

Regarding the prior art, the following publications, which are directed to solid dosage forms distinguishable from conventional tablets are noteworthy. Russell, U.S. Pat. No. 3,444,858 issued May 20, 1969 describes a vehicle for the buccal administration of medicaments comprising a strip of gelatinous material containing medication, said strip being divided into sections each of which is connected to the next by easily tearable ligaments. In use, a section is merely separated from the strip and placed in the mouth.

A second publication warranting mention is an article in the New England Journal of Medicine, Vol. 289, No. 10 pp. 533–5 (1973). This article describes a means whereby birth control medication is being made available to women in the Peoples Republic of China on a very large scale. In this method, a sheet of colored, water-soluble, carboxymethylcellulose paper is treated with a solution of progestational and estrogenic materials. The sheet is then perforated and cut into strips. The medicament is packaged as a strip of 22 "squares" which are torn from the strip and taken daily. This method does not provide for the concealment of the drug in the final dosage form, thereby suffering from the disadvantage of potential contamination and/or inactivation of the medication once the package is opened. Further, by virtue of not being completely unitized, such perforated strips can give rise to uneven tearing at the perforations and potentially, disproportionant dosage.

Finally to be considered is Higuchi et al. U.S. Pat. No. 3,625,214 issued Dec. 7, 1971 which describes a dosage form utilized for controlled, i.e., sustained release of medicaments. The dosage form is comprised, in essence, of a medicament containing matrix which is coated on a substrate which is then spiral wound to a final "jelly roll" appearance. After ingestion, the medicament is released by the gradual erosion of the outer layers of substrate and also by diffusion from the sides where there is exposed medicament. There is no disclosure of whether the disclosed dosage forms are amenable to high capacity pharmaceutical manufacturing. There is further no disclosure of means whereby the disclosed dosage forms can be rendered into pharmaceutically elegant finished products.

In distinct contrast to the teachings of the foregoing publications, the novel solid dosage units of the present invention are completely utilized, amenable to non destructive, on-line analytical testing during high capacity pharmaceutical manufacturing operations, are essentially free from pharmaceutical adjunct materials that may interfere with performance, have no exposed medicament and have a superior consistency of release of medicament which enhances the efficacy thereof.

BRIEF STATEMENT OF THE INVENTION

Solid, unit dosage forms primarily for oral administration comprising an edible web of paper and/or polymeric materials having deposited thereon or at least partially thereon one or more medicaments having essentially no pharmaceutical adjunct materials admixed therewith, said web being fabricated into an ingestible; pharmaceutically and cosmetically acceptable shape and sealed so as to have no exposed medicament are disclosed. The unit dosage forms are prepared by high capacity pharmaceutical manufacturing techniques utilizing, in certain instances, novel apparatus. The manufacturing process includes means to non-destructively test the dosage forms on-line to determine the amount of medicament which has been loaded to the web prior to the fabrication thereby assaying the potency of the finished dosage units by physical parameters.

DETAILED DESCRIPTION OF THE INVENTION

The present invention is directed to solid, unit dosage forms primarily for oral ingestion which are advantageous in a number of particulars over present solid oral dosage forms, i.e., tablets and capsules. First, the fact that the dosage units of the invention are substantially free of conventional pharmaceutical adjunct materials results in a savings in cost of raw materials and manufacturing procedures as well as eliminating potential incompatibilities caused by the presence of such materials. The distinction must be made here between the webs of the invention which can be considered adjunct material and the materials such as fillers, binders and the like which are admixed with the medicament in conventional solid dosage forms.

Second, because the solid unit dosage forms of the invention are prepared continuously and subjected to on-line, non-destructive analytical procedures, the requirement for batch lot manufacturing as it is known today is eliminated thereby realizing a considerable economic saving and a substantially improved level of quality control viewed in terms of the finished dosage units. The fact that the manufacturing operation of the invention includes means to feed back information from a testing station to the manufacturing procedures immediately preceeding it thus affording on-line corrections and adjustments. Such means facilitate the removal of only a small number of dosage units from any number designated as a manufacturing lot, i.e., from the positive reading immediately preceding a negative reading to the next following positive reading. The designation and removal of such small quantities of dosage forms thus avoids "poisoning of the barrel" and realizes both a large economic advantage over present pharmaceutical manufacturing procedures and a superior level of quality control particularly in terms of the active ingredient content in the finished dosage forms.

In normal operation, the dosage form of the invention are manufactured by time lot procedures, i.e. a "lot" of dosage forms constitutes the number prepared between two given points in time. This concept is believed to be unique in the pharmaceutical industry. It will be appreciated, however, that some destructive testing will be required in any pharmaceutical manufacturing procedure as a check of performance of the finished product. Such testing is, however, required to a materially smaller degree in the procedures of the subject invention than in conventional manufacturing operations. More important, however, is the fact that such destructive procedures, i.e., performance evaluation are carried out on-line with the information feed back thus realizing the benefits discussed above regarding the non-destructive procedures.

Third, the solid oral dosage units of the present invention are unique in that they differ from conventional tablets and capsules in appearance, shape, texture, etc. and therefore have the advantage of being easily identified. Also, the on-line non-destructive testing procedures and continuous manufacturing operations of the present invention facilitate packaging of the unit dosage forms of the present invention on-line into individual containers such as, for example, clear plastic strips of blister packages thereby saving costs in handling and equipment.

Fourth, the exactness of the preparation of a solid dosage forms of the present invention, i.e., the uniformity of deposition of the medicament on the web and the precision in shaping of the final units combined with the desirable characteristics of the web itself enable the finished dosage forms to easily meet stringent specifications, of size, shape, release of medicament and the like. The dosage forms of the invention also possess excellent stability and are amenable to the incorporation of medicaments which are recognized as being adversely affected by moisture since, in certain embodiments of the present invention, the medicament is deposited or loaded to the web by electrostatic deposition thereby providing an almost total absence of moisture which might cause an adverse reaction to take place. Also, wherein the dosage forms of the present invention are fabricated from a laminate of sheets of web, medicaments recognized in the art of pharmaceutical compounding as being chemically imcompatible can be deposited upon alternate sheets of web. This effectively stabilizes such combination without the need to resort to such economically unattractive measures as the coating of one or more of such incompatible substances with an insulating material, the admixture of stabilizing adjunct materials with such medicaments, the incorporation of such medicaments into separate tablet layers which are then pressed together and the like. Because of either or both of these procedures, i.e., the deposition of a medicament on the web electrostatically as a dry powder and the placing of potentially incompatible medicaments alternately between sheets of a laminate, the dosage forms of the invention are advantageously useful in the administration of effervescent formulations.

The solid oral dosage forms of the present invention are further unique in that the medicament contained therein is completely internalized within the dosage form yet, in most instances, there is no coating per se applied to the finished dosage form. This represents an additional economic advantage for the dosage forms of the subject invention over conventional tablets which must be coated to obtain internalization of the medicament.

While the dosage forms prepared in accordance with the methods of the present invention are intended primarily for oral administration, dosage forms suitable for rectal and/or vaginal administration are likewise contemplated. Modifications in the size of the web as well as the fabrication methods to be described hereinafter to produce dosage forms of the desired size and shape will be readily apparent to those skilled in the art. Certain modifications of the web composition to obtain the desired type and pattern of release of medicament would likewise have to be made. Tests have shown that rectal and vaginal insertion of solid dosage forms according to the invention has produced substantially no local irritation.

As mentioned above, the novel dosage units prepared in accordance with the invention can be formulated or "engineered" to any desired release pattern including sustained release. Regardless of the release pattern, the dosage units of the invention are characterized by an exceptional uniformity of release over a large number of dosage units, e.g., 10,000 or more. The variance in release rate can be obtained in accordance with the present invention by the manipulation of a number of factors such as, for example, the thickness of the web, the composition of the web, the presence of an overwrap or outside seal on the fabricated web and its composition, how tightly the web is fabricated, and the like. For example, a web composition containing a high content of sodium carboxymethylcellulose will normally disintegrate slowly in gastric fluids. Dosage forms fabricated from such webs by fan-folding as will be described hereinafter will open or unfold upon contact with gastric fluid thereby releasing the medicament loaded on the internal surfaces thereof very rapidly, in fact, more rapidly than conventional tablets and capsules presently available. However, if such a fan-folded dosage form were to be sealed on the folded edges with a substance such as, for example, ethylcellulose, cellulose acetate phthalate or zein which will prevent its opening in gastric fluids, the medicament would become available by the gradual erosion of the web thereby giving a steady, sustained release of medication. Since the dosage forms prepared in accordance with the present invention are capable of releasing medication with a rapidity superior to presently available solid dosage forms, i.e., tablets and capsules, such release represents the preferred embodiment of the present invention.

The accompanying drawings are summarized as follows:

FIGS. 4, 4A and FIG. 5 illustrate the rotary-forming and lamination techniques of dosage form fabrication.

THE WEB

Figure 1:
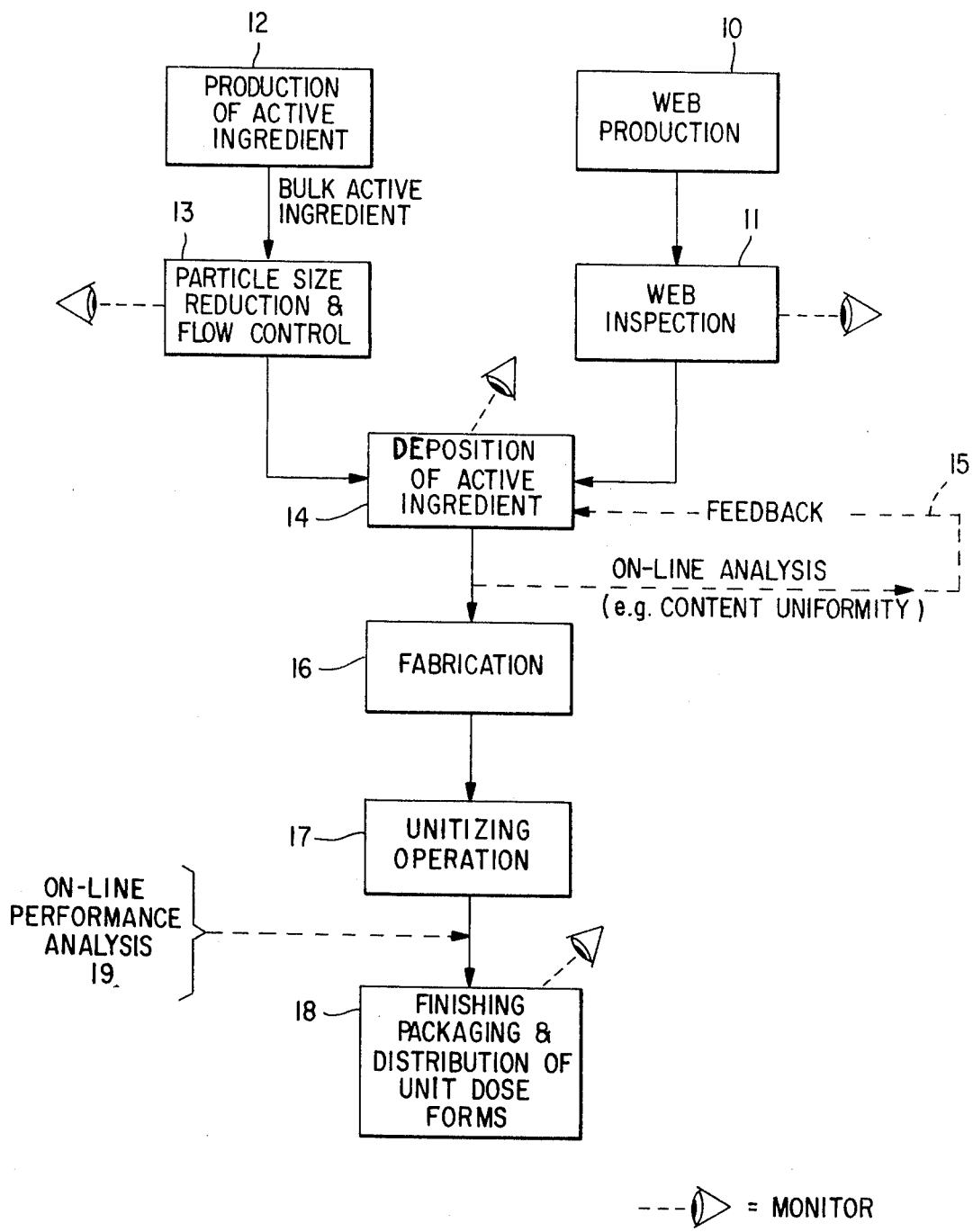
FIG. 1 is block diagram of the total manufacturing process indicating points of on-line inspection.

The webs capable of being utilized for deposition for medicament in accordance with the present invention must meet a large, diverse number of physical and chemical criteria to be acceptable in the practice of the invention. These criteria can be briefly summarized as follows:

The web must be non-toxic, edible and, particularly, not have an objectionable "feel" in the mouth. In addition, the web preferably self destructs or is degradable in body fluids and/or enzymes. However, the web can be of non-destructible substance which is readily eliminated by the body. The web preferably is hydrophilic and readily disintegrable in water. These properties must not be adversely affected and, preferably, be enhanced at the pH of gastric fluid;

The web must be totally inert to the medicament loaded thereto and must not release any substance upon dissolution with gastric fluid which would cause an in situ incompatibility with said medicaments;

The web must be stable over extended periods of time and at elevated temperatures and relative humidity and generally be a poor medium for the growth or microorganisms;

The web must have acceptable resistivity properties so that powdered medicament (usually possessing dielectric properties) can be loaded thereto by electrostatic deposition;

The web must possess acceptable workability and mechanical properties, i.e., it must possess sufficient elasticity to allow it to be drawn or cast into a thin sheet, i.e., from about 0.025mm to about 0.25mm in thickness, it must possess good tensile strength and tear strength and it must have acceptable fold endurance where required to withstand certain of the fabrication methods as will be described hereinafter;

The web surface must facilitate the types of on-line analytical procedures described hereinafter, be capable to being coated with and retain powdered medicament electrostatically or otherwise loaded thereto and be amenable to printing operations;

The web must be readily sealable by liquid and or heat seal methods such as are recognized in the art. The sealing, however, must be effective at levels of moisture and heat which do not adversely affect the medicament contained in the dosage form. In addition, the web must possess acceptable flammability resistance so as to tolerate such sealing operations;

In certain instances the web must possess "memory", i.e., it must have sufficient resiliency so that, upon contact with gastric fluids, it will very rapidly reverse the fabrication process and "open" thus releasing medication for absorption. By "opening" is meant that, for example, if the dosage form is fabricated by fan-folding it will open like a bellows, if fabrication is by convolute winding it will uncoil, and the like; and The web must possess other properties such as, for example, having acceptable taste and odor which will become apparent to those skilled in the art from the instant disclosure.

As mentioned above, the webs utilized in the present invention are preferably water soluble or water dispersible. There are two basic mechanisms whereby the webs of the present invention are formulated to self destruct in contact with water or gastric fluid. First, the web can contain particles of substance such as, for example, casein, gelatin and the like which swell upon contact with water thereby disrupting or breaking the web. Second, the web formulation may contain both water soluble and insoluble constituents. Upon contact with water, the soluble constituents of such a formulation will tend to go into solution and the insoluble constituents to precipitate thereby causing the web to rupture. The latter means of disrupting the web is not as rapid as the former. Examples of suitable water soluble constituents include methylcellulose and the like. Examples of suitable water insoluble constituents include ethylcellulose, and the like.

The web formulations utilized in preparing the novel dosage forms of the present invention are of two basic types, i.e. polymeric and paper. The polymeric formulations generally comprise;
  a. one or more organic film formers
  b. one or more plasticizers
  c. modifiers, i.e. other ingredients optional with certain formulations such as distintegrants, extenders and the like,
  d. in one or more fugitive solvents. The paper formulations generally comprise:
  a. one or more fibrous materials
  b. one or more non-fibrous modifiers, i.e. other ingredients optional will certain formulations, e.g., one or more organic film formers, disintegrants, extenders and the like,
  c. in a fugitive solvent.

The film forming compound of the polymeric webs of the present invention comprises one or a mixture of art-recognized, non-toxic, organic film formers such as, for example, natural and chemically modified starches and dextrins, proteins such as gelatin; cellulose derivatives such as sodium carboxymethylcellulose, hydroxypropylmethylcellulose, hydroxyethylcellulose and the like; other polysaccharides such as pectin, acacia, xanthan gum, guar gum, algin and the like; synthetics such as polyvinylpyrrolidone, polyvinyl alcohol and the like. Preferred film formers are hydroxypropylcellulose and sodium carboxymethylcellulose. Although the concentration of the film forming component in the polymeric web is not particularly critical to the practice of the invention, it has been found that between about 5 by weight and about 95% by weight is preferred with a concentration of from about 40% by weight to about 90% by weight being most preferred.

The above named film forming substances are equally illustrative of the film forming component of the paper web formulations of the present invention where such is present. Preferred film formers of the paper web formulations of the invention are likewise hydroxypropylcellulose and sodium carboxymethylcellulose. The concentration of the film forming ingredient in the paper web formulations of the invention is likewise not considered critical. However, when such ingredient is present to act as a binder or disintegrant for the fibrous material, it should not exceed about 40 by weight, preferably from about 2% by weight to about 20% by weight and most preferably from about 4% by weight to about 10% by weight.

The fibrous ingredient of the paper web formulations of the invention can be any of the commercially available natural or artifical fibers which have been shown by proper tests to be non-toxic. Examples of such fibers include cotton, linen, cellulose, synthetically modified cellulose, rayon, textured vegetable protein, collagen and the like.

To insure the required workability and mechanical properties, the polymer webs utilized in the practice of the invention contain an effective amount of a plasticizing ingredient. Such ingredient may include one or more members of the group of plasticizers recognized in the art of pharmaceutical compounding such as, for example, glycerin, the polysorbates, e.g., polysorbate 80, polysorbate 60, certain mixtures of mixed mono- and di-glycerides of saturated fatty acids and the like. It is preferred that such plasticizers be present in an amount comprising from about 1 by weight to about 60% by weight, preferably from about 10 by weight to about 50% by weight of the web composition.

Both polymer and paper webs may contain one or more disintegrants such as are recognized as being conventional in the art of disposable paper such as, for example, various types of starches, casesin, gelatin and the like. The webs according to the invention should contain from about 0% by weight to about 40% by weight preferably from about 5 by weight to about 20% by weight of disintegrant depending on the web formulation.

Further, both types of web formulations may contain one or more fillers or extenders which are recognized in the art as being conventional. Such ingredients include, for example, opacifier fillers such as titanium dioxide, chalk, kaolin and the like, microcrystalline cellulose, calcium carbonate and the like. It is to be appreciated that some of the ingredients enumerated herein can function in more than one capacity and therefore fall under more than one of the categories listed above. For example, calcium carbonate can function as both an opacifier and dispersant, certain starches can function as binders and as disintegrants, etc.

In addition, both polymer and paper formulations may contain one or more modifying ingredients which affect the electrical, mechanical, optical or permeative properties of the webs produced therefrom. Examples of such ingredients would include an electrolyte such as, for example sodium chloride, potassium chloride and the like, surface active agents such as dioctyl sodium sulfosuccinate and the like. The webs may also contain optional ingredients such as pharmaceutically acceptable coloring agents, preservatives, and the like.

Finally, both types of web formulations, in most instances, will contain a fugitive solvent, e.g., water, certain organic solvents, for example, ethyl alcohol or combinations of such solvents i.e., a hydroalcoholic mixture which is removed during formulation of the web.

Specific examples of film compositions in accordance with the present invention include the following:

Polymeric films that self-destruct in an aqueous environment due to the presence of swelling agents.

| Ingredient | Percent by Weight |
| --- | --- |
| I Hydroxypropylmethyl-cellulose | 45.69 |
| Acacia | 19.44 |
| Gelatin, extra fine, solubilized | 32.08 |
| Dioctyl Sodium Sulfosuccinate 75% aqueous solution | 0.09 |
| Titanium dioxide | 1.94 |
| Lecithin | 0.75 |
|  | 100 |
| II Refined starch | 33.06 |
| Carboxymethylcellulose | 33.06 |
| Propylene Glycol | 33.06 |
| Sodium Benzoate | 0.55 |

-continued

| Ingredient | Percent by Weight |
|---|---|
| Sorbic Acid | 0.28 |
| | 100 |
| III Hydroxypropylmethylcellulose | 55.19 |
| Cellulose Acetate Phthalate | 2.99 |
| Corn Starch | 28.66 |
| Propylene Glycol | 9.87 |
| Titanium Dioxide | 1.52 |
| Dioctyl Sodium Sulfosuccinate | 1.52 |
| Lecithin | 0.25 |
| | 100 |
| IV Hydroxypropylmethyl-cellulose | 64.00 |
| Cellulose Acetate Phthalate | 3.10 |
| Calcium Carbonate | 21.74 |
| Propylene Glycol | 9.06 |
| Titanium Dioxide | 0.91 |
| Dioctyl Sodium Sulfosuccinate | 0.91 |
| Lecithin | 0.30 |
| | 100 |

All of formulations I–IV are sealable by the application of heat and pressure. Formulation IV self destructs in an aqueous environment due to the presence of insoluble polymeric agents.

Preferred paper formulations in accordance with the subject invention comprise from about 70 by weight to about 99% by weight, preferably from about 90 by weight to about 96% by weight fiber, e.g., hardwood or softwood fibers or mixtures thereof, from about 1 by weight to about 30% by weight, preferably from about 4 by weight to about 10% by weight of distintegrant selected from the group consisting of sodium carboxymethylcellulose, methylcellulose, hydroxypropylcellulose, polyvinylpyrrolidone and guar gum and from about 0 by weight to about 5% by weight, preferably from about 0 by weight to about 2% by weight of a surfactant such as, for example, polysorbate 80, dioctyl sodium sulfosuccinate, sodium lauryl sulfate and the like. The ability of the above substances to function as disintegrants in paper formulations is considered to be unexpected in view of the fact that, where members of this group are utilized in paper making they are present in different quantities and perform a different function. For example, wherein sodium carboxymethylcellulose has heretofore been utilized in paper making, it has been utilized in small quantities, i.e. 0.1% by weight or less as an aid in dispersing the fibers as the paper is formed. In distinct contrast, it has been found that when sodium carboxymethylcellulose or the other substances enumerated above are added in large quantity, i.e. up to 30% by weight after the paper web is formed but while it is still wet they will function as disintegrants the time of addition of these substances is critical to the function thereof as disintegrants. The disintegrants are added as a solution preferably in the solvent utilized to prepare the paper web. It has been found that the above named disintegrants, when added to the web as herein described, coat the fibers. When the finished dosage form is contacted with water, the disintegrant swells thus forcing the fibers to disrupt the web. The surfactants, where present, acts to enhance the penetration of water to the disintegrant thus promoting disruption.

The webs utilized in accordance with the invention are formed by processes conventional in the arts, e.g., the paper-making and film making industries. For example, the polymeric webs can be cast on an appropriate substrate, e.g., Mylar, stainless steel, release paper and the like. The webs are then dried, e.g., in a forced-air oven. The temperature of the drying air and length of drying time depend on the nature of the solvent utilized as is recognized in the art. Most of the webs contemplated herein, however, are dried at a temperature between about 25° and 105°, preferably between about 60° and 90° C.

A second method of forming polymeric webs which is conventional in the art is extrusion. This method is preferred with webs wherein the film forming ingredient is a modified food starch, hydroxypropylcellulose or other extrudable polymer. The mechanical particulars of the extrusion process, e.g., the particular equipment utilized, the extruding force, the shape and temperature of the orifice are considered to be within the skill of the art and can be varied in a known manner to achieve the physical characteristics of the webs to be described hereinafter.

The paper webs of the subject invention are prepared utilizing conventional paper-making machinery such as, for example, Fourdrinier paper making machines. In all cases, however, the web must be uniform in both thickness and width. The webs are between about 1 and about 10 mils (about 0.003mm to about 0.03mm), preferably from about 1.5 to about 4.5 mils (about 0.38mm to about 0.123mm) thick. A convenient width for such webs is 12 inches (30cm) although the width of the web is not particularly critical to the practice of the invention. The web can be produced in any length. However, in view of the fact that the novel dosage forms produced in accordance with the invention are emminently suited to high speed manufacture, the webs should be prepared in large quantity, e.g., 15000 feet or more which can be stored, e.g., on cores or spools.

Reference is made to FIG. 1 in which is shown in block diagram form the overall system process for manufacturing in large numbers the various kinds of dosage forms herein described. Block 10 of FIG. 1 represents web production from formulations such as have been discussed above. As the web is produced, or shortly thereafter, it undergoes an inspection step (block 11 in FIG. 1) where various examinations, which may be in whole or in part automated, are performed, to ensure the integrity of the web, as will be more particularly described hereinafter. It is to be noted, however, that the inspections of the web can take place as the web is formed or at any convenient point thereafter, either by means associated with the apparatus making the web or by other apparatus, and may, in fact, be performed at another location.

Figure 2:
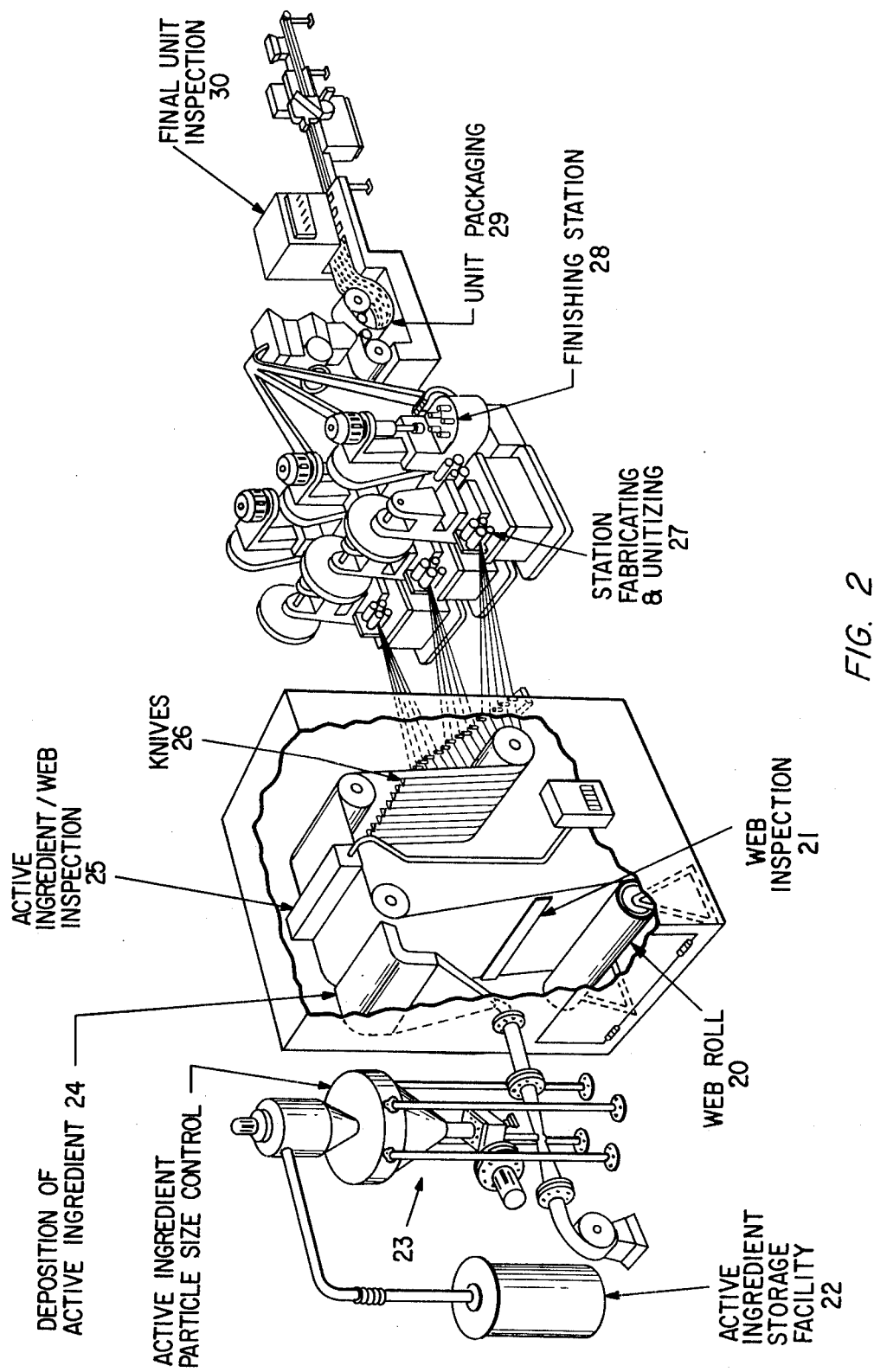
FIG. 2 is a diagrammatic representation of a system capable of effecting the process depicted in FIG. 1.

The active ingredient to be deposited on the web is prepared and stored for use in container means, as is generally illustrated at 23 in FIG. 2, which figure illustrates, largely in schematic form, the various apparatus suitable for performing the steps indicated in FIG. 1. The prepared active ingredient is caused to be forwarded to an arrangement generally indicated at 23 in FIG. 2 where the active ingredient particle size reduction and control indicated at step 12 in FIG. 1 is performed. Although this step will be discussed in greater detail hereinafter, it is intended via this step 13 and the depicted apparatus 23 to provide a uniformity of flow in order to enable exact and uniform deposition (block 14 of FIG. 1) of the active ingredient on the web, which is illustrated at 24 in FIG. 2. It should be noted that the system example depicted in FIG. 2 pertains to the deposition of dry particulate material onto the web in a dry state. It is to be clearly understood, however, that the scope of this invention includes as well wet deposition of active ingredient onto the web. FIG. 2 also illustrates schematically at 21 that embodiment of the invention wherein the web is prepared and stored for later use, i.e., the web inspection step (Step 11 of FIG. 1) is performed, e.g., as the web is caused to be taken off of a storage roll 20. It is to be clearly understood that inspection may be made prior to the web being wound and stored as well as or in addition to being performed where and as indicated in FIG. 2 at 21. The particulars of web inspection are described in greater detail hereinafter.

With more particular regard to inspection means 21, inspection of the uncoated web is accomplished by several methods. Holes, blemishes, and physical integrity of the web may be evaluated and quantified by using a scanning laser beam and photodetector combination. The system is used in both transmission and relection modes. The continuous helium-neon laser beam is steered across the web by a mirror on a galvanometer. The mirror position is electronically controlled so that the position of any defect on the web can be located. The reflected or transmitted light is detected by a linear photodiode located behind an interference filter to exclude room (stray) light. The electrical output is used to count the number of defects and determine their size and distribution along the length of the web. This is accomplished by analyzing the detector output signal with a pulse height-width analyzer.

An alternate method capable of inspecting the web at significantly higher web speeds is a parallel array of photodiodes positioned across the web. Each photodiode has its own threshold detector system and digital logic which allows a low-resolution defect size and position location characterization. The output signal can be processed to yield approximate size distribution and the location of the defects on the web.

The physical thickness of the web is measured by a parallel array of web riders mounted in precision bearings. These rollers contact the web and are connected to transducers which electronically sense position to at least 1/10,000 inch. A similar system of physical thickness can be made of pneumtic sensors which float above the web on a fixed film of air. This system has the advantage of noncontact with the web.

Mass thickness (weight per unit area) or basis weight of the webs is determined by using a noncontacting beta-ray or x-ray gauge. These systems measure the absorption of beta-rays or x-rays passing through the web. This absorption is related to mass thickness. In an alternate system, the electrical resistance between two contacting web-riding electrodes may be used to determine the basis weight of webs with known moisture content.

On-line analysis of moisture content can be measured by one or more of the following methods. First, the high dielectric content of water allows sensitive moisture determination to be made by direct microwave absorption and by radio-frequency dielectric constant sensors. Low-frequency conductance measurements can also be used to measure the amount of web moisture. Infrared spectrophotometric absorption provides a totally independent moisture measuring method. Further, the optical absorption at wavelengths in the region of 1-2 micrometers will yield a specific and precise moisture determination in a spectral region wherein the web being inspected is relatively transparent.

The web, having passed the inspection means 21, is guided by a suitable roller arrangement shown in FIG. 2 to pass in close proximity to the active ingredient deposition apparatus 24 wherein active ingredient is loaded to the web. The deposition apparatus is immediately followed by means 25 schematically shown for on-line analysis/inspection, e.g., for content uniformity of active ingredient, of the coated web preferably as a single sheet before the active ingredient has been internalized.

A preferred method for the nondestructive on-line analysis of active ingredient deposited on webs is x-ray absorption. In this method, low energy x-rays peaked to match the absorption edge of atoms deposited on the web are directed through the coated web. The absorption of the x-rays is related to the active ingredient-plus-web absorption. Wherein the active ingredient is deposited on the web by a wet-coating process, this method of analysis may be utilized either before or after the drying step.

Since the total x-ray absorption arises from the combination of web and active ingredient containing coating, it is necessary to determine the absorption of the web separately. This is accomplished by means of a beta-ray gauge or an infrared spectrophotometer. Increasing sensitivity is achieved for the x-ray measurement of deposited active ingredient containing atoms with increasing atomic numbers. The x-rays source can be tuned by varying the accelerating voltage to match the absorption edge for many atoms of interest.

Reflectance or transmittance spectrophotometry may also be utilized to nondestructively analyze the deposited active ingredient on-line. Reflectance spectrophotometry is used in the near ultraviolet region to determine active ingredient loading. This technique may be used with any solid active ingredient having an optical absorption in a suitable wavelength region.

Transmission spectrophotometry may also be used for nondestructive on-line analysis of active ingredient coated on webs. A suitable light source, monochromating element, and detector combination are selected for wave-length regions where the active ingredient selectively abosrbs. This must be in a spectral region where the web itself does not strongly absorb. Such regions for webs of the present invention occur in the near-infrared and functional group infrared regions of the spectrum. A rapid wavelength scanning system is used to sweep over a small wavelength region of interest. The signal from the detector is time-averaged over several scans to reduce the effects of noise. The signal data are then processed to give a first derivative of transmission with respect to wavelength for increased sensitivity. This is done in a similar fashion for other wavelength regions which are sensitive to other components in the system. Thus water content, basic weight of the web as well as active ingredient content can be determined simultaneously.

Another method for analysis of active ingredient loading is molecular fluorescence. Excitation radiation in the ultraviolet or visible region of the spectrum is provided by a suitable filter combination. The fluorescence from the active ingredient is detected by a wide-band filter-detector combination matching the fluorscence peak; a blocking filter is used to remove the excitation energy. The detector for this method is preferably a photon counter, which counts individual photo events, providing high sensitivity and linearity at low levels of illumination. In this method of analysis, precautions must be taken to limit the photodegradation of the active ingredient by the excitation radiation.

The coated web may be stored for a time or, preferably, directly forwarded to means for fabrication (step 16 of FIG. 1) and unitizing (step 17 of FIG. 1) to form dosage forms which means are illustrated in FIG. 2 as a series of knives 26 for slicing the coated web into a multiplicity of endless strips, followed by fabricating and unitizing means 27 of the lamination type, i.e., the endless strips are stacked one on another to form an endless stack which is pressed ultimately unitized in accordance with the invention as hereinafter described.

The unitized dosage forms are then finished and packed by appropriate apparatus (step 18 of FIG. 1) schematically illustrated at 28 and 29 in FIG. 2, for subsequent distribution. Appropriate inspection (at e.g., 30 in FIG. 2) is performed in connection with this step. The purpose of the final inspection of individual dosage units is to verify size, shape, integrity, identity, presence and accuracy of printing, and active ingredient content. All of this inspection is done non-destructively except for active inredient content. In order to analyze for active ingredient content and performance characteristics, a statistically appropriate sample of dosage units is removed from the production line and destructively analyzed both for potency and performance, e.g., dissolution characteristics, by solution spectrophotometry as will be discussed hereinafter.

An optical scanning system may be used to inspect all the production units for size, shape, integrity, identity, and the presence and accuracy of printing. The system comprises a suitable light source and a matrix of photo-detectors or a T.V. camera. A computer is used to process the signals from the optical system. Suitable algorithms are used to determine the acceptability of the dosage units. Another method employs a comparison of the sample image with a standard image by means of an image-masking technique.

In another method for 100% inspection, an optical transform of the image of the dosage unit is made. The Fourier transform spectrum, the power spectrum, or other suitable transform is compared with a similar transform of a standard by means of a computer.

Prior to the finishing step, step 19 (FIG. 1) of on-line analysis for dissolution and content uniformity is performed by suitably arranged apparatus not particularly illustrated, which apparatus may include and/or by controlled by computer or similar central processing or logic means. A random sampling mechanism removes one dosage unit at a time from the end of the production line at a rate of 25 to 120 units/min., preferably at a rate of 40–60 units/min. Each unit is sequentially transferred to a conventional automatic weighing device wherein it is weighed by nondestructive means and the information stored. Randomly-selected units are then sequentially placed in a conventional automatic analyzing system. The dosage unit is stirred in a suitable solvent for the active ingredient at an appropriate rate. The amount of active ingredient dissolved at $t_j$ minus the amount dissolved at $t_i$ divided by $t_j-t_i$ is taken as the rate of dissolution. The appropriate time interval ($t_j-t_i$) has been previously chosen and will vary with individual medicaments. A suitable time interval might range from 5 seconds to 2 minutes or more. The sample is then continuously stirred for a sufficient time to allow for all of the active ingredient to be dissolved after which the solvent is analyzed for content of active ingredient. The amount of active ingredient in this analysis plus the amounts from samples $t_i$ and $t_j$ is the total present in the dosage forms. This information is also recorded and stored. If the weight, thickness, dissolution rate, and analysis of the medicament content fall within previously defined limits, the units are deemed acceptable. If the readings do not fall within these limits, the units produced beginning with the negative analysis and ending with the next positive analysis are quarantined for further evaluation.

It is to be noted in FIG. 1 that further provision is made for monitoring functions to be performed in accordance with this invention as are described hereinafter. Regarding the web inspection step, it is intended, for example, that continuous monitoring inspection of the web be made from the standpoint of the web color, thickness, continuity, soil spots and defects of virtually any kind. These functions may be performed by electronic and/or optical instruments as well as by visual observation.

Inspection of the web includes the actual placing of a "flag" on the web wherever a fault or defect is detected. Additionally, apparatus may be provided such that, whenever a defect is detected in the web a printout is generated, either automatically or under operation control, indicating that on the web at certain distance downstream a defect of some sort exists, which printout would include an identification of the type of defect, such as a hole, blackspot, blemish etc..

The means for generating the printout can be the same apparatus actually flagging the web per se. Such apparatus is considered conventional in fabric manufacturing and fabric inspection, for example, with the exception that the handling and inspection of the web would, in the instant case, be performed in accordance with good manufacturing practices.

In addition, by the same or additional conventional inspection apparatus the web thickness would be measured. This could take the form of a visual display involving an operator or could be a detecting device coupled to a logic arrangement having upper and lower limits for web thickness, wherein if the thickness of the web violates one of the limits, there will also be effected a printout and a flag placed on the web as described above. One form of apparatus for providing thickness measuring of the web could take the form of an x-ray or a beta ray gauge or some similar device for measuring the mass thickness of the web.

In the case of step 13 of FIG. 1 regarding particle size reduction and flow control, it is intended that monitoring functions be performed as described in the following. In accordance with the invention, notwithstanding that the unloaded web itself has been monitored for defects and thickness, similar monitoring is contemplated following loading of the web with active ingredient(s). For example, x-ray gauge apparatus would, again, be applicable to determine the loaded web thickness, which thickness, in comparison to the earlier determined unloaded web thickness, would enable conclusions to be derived regarding the amount of active ingredient loaded to the web. Additionally, it is within the scope of this invention to provide actual mass monitoring means in order to determine the amount of active ingredient loaded to the web. It should be understood that performance of coated-web inspection could be effected by routing the coated web back through the same apparatus performing the web inspection in connection with step 11 in FIG. 1.

The active ingredient deposition system (reference 14 in FIG. 1) is controlled by feedback from the on-line analysis of active ingredient content on the web. For example, electrical signals from the on-line analyzer (digital) or analog) analyzing active ingredient loading (weight of active ingredient area of coated web) are used in a feedback mode (reference designator 15 FIG. 1) to control the amount of active ingredient applied to the web in the deposition process. These feedback signals are fed, for example, to a minicomputer which produces a suitable signal to the deposition process. The correction signal causes either an increase or a decrease in the active ingredient loading so as to maintain the loading within a narrow range around the target value. For example, in the dry deposition process, the active ingredient powder is introduced into the deposition apparatus. Thus, the correction signal is used to control the feed rate and, consequently, the active ingredient loading.

In the wet deposition process, the correction signal may be utilized, for example, to vary the amount of the coating formulation which is applied to the web. For example, the gap between metering rollers or between a metering knife and application roller is varied to change the active ingredient loading. In reverse roll coating, the rotational speed of the application roller is varied to change the active ingredient loading. Another means of control in wet deposition is by variation of the concentration of active ingredient in the coating liquid. Two liquid formulations containing different concentrations of active ingredient are mixed in the required proportions to supply the correct concentration; the ratio of the two formulations may then be varied to accurately control active ingredient loading.

DEPOSITION OF MEDICAMENT ON THE WEB

The methods of "incorporating" active ingredient into the novel dosage forms of the present invention constitute a radical departure from methods of incorporation active ingredients into conventional solid dosage forms, e.g., tablets, capsules, dragees, suppositories, etc., While the methods and equipment utilized in the methods of the invention may vary somewhat, the overall prime object is uniformity of deposition, i.e., to deposit active ingredient on the moving web surfaces in an exceptionally uniform manner. The manner of active ingredient deposition utilized in accordance with the present invention is unique and possesses a number of advantages over manufacturing procedures commonly utilized in the pharmaceutical industry.

In view of the fact that the active ingredient is deposited on or substantially on the surface of an edible web which is then fabricated to completely internalize it, there is no need for common pharmaceutical excipients, fillers, preservatives and the like to be admixed with the active ingredient thus eliminating a cost and, more importantly, a source of potential incompatibilities and quality control problems. The web, in accordance with the present invention, is loaded with a uniform coating of active ingredient and is then divided into individual dosage forms by linear or geometric subdivision thereby effecting a level of uniformity of strength of active ingredient over a large number of dosage units which is substantially superior to the batch requirements now accepted in the pharmaceutical industry. In distinct contrast, conventional pharmaceutical manufacturing operations require that the active ingredients and suitable therapeutically inert pharmaceutical adjunct materials are prepared in a large quantity and subdivided volumetrically for filling into capsules or compression into tablets. Utilizing the manufacturing methods of the present invention, it is therefore possible to reduce the amount of excess active ingredient present to assure label dosage from the presently accepted level of from 5 to 10% by weight to approximately 1 to 5% by weight thereby realizing a substantial saving particularly when compounding very expensive active substances, e.g., certain hormones and antibiotics. Finally, the method of depositing or loading the active ingredient to the web in accordance with the present invention allows for continuous, on-line, non-destructive testing of the dosage by physical parameters thereby facilitating superior uniformity of amount of active ingredient over a large number of dosage forms.

The active ingredient may be loaded to the web in either wet or dry form, with dry form being preferred. In either instance, the active ingredient is deposited in a form susceptible to analysis as will be described hereinafter, i.e., a finely particulate form. The particle size is in the submicron range and can also be within a narrow size range from 1 up to 100 microns. Particles in the submicron range have heretofore been considered as being too fine for the production of pharmaceutical tablets without first being subjected to techniques such as granulation which substantially increases particle size and which also adds excipient matter to the active ingredient. The technology of the invention facilitates the use of such ultrafine particles without the need to resort to such techniques and/or the addition of excipient matter. The active ingredient is deposited as a very uniform coating on the web as it is being moved in an automated manufacturing system.

The preferred method of deposition of active ingredient on the web wherein the active ingredient is a dry form is powder cloud electrostatic deposition utilizing techniques generally recognized in certain non-pharmaceutical arts. Generally, this method requires passage of the web through an electrostatic field in a suitable chamber. Finely particulate active ingredient is charged as it is introduced into the chamber via, for example, a forced air stream and is deposited on the web as it passes over an oppositely charged roller. It is readily apparent that this is an oversimplification. However, apparatus required to accomplish this result is known in certain non-pharmaceutical fields such as the production of adhesives and adhesive papers. For a successful deposition to take place, it will be apparent that the web must have a resistivity capable of enabling the deposition thereon of dielectric particles. Additives which can be present in the web formulation to enhance the proper electrical properties thereof have been discussed above. In a number of instances, it has been found that, prior to electrostatic deposition of active ingredient powder, it is necessary to coat the web with a substance which will enhance the adherence of the powder thereto. Examples of such substances include carboxymethylcellulose, methylcellulose and the like. These adherence enhancing substances may be applied to the webs in a conventional manner, e.g., by applying a solution in a fugitive solvent such as water and drying with, e.g., heated air. The application of a coating to the web to insure adherence of the active substance is then immediately followed on-line by the coating or "loading" of the web with active substance. The adhesive is then activated to bind the particles of active substance to the web. This is accomplished by applying heat, pressure, moisture or a suitable combination thereof to the loaded web. In addition to the electrostatic powder cloud deposition method, fine particulate active ingredient may be coated onto the web in a dry state by Electrogasdynamic Powder Coating. In this method, the particles of active ingredient are electrically charged by exposure to corona discharge and propelled by a gas stream into an electrically insulated chamber. The web is passed through this chamber on a metallic surface which is either grounded or charged with opposite polarity to that of the charged cloud of particles of active substances. The electric field between these particles and the metallic surface attracts them to the web and deposits them thereon.

Further in accordance with the present invention, active ingredient may be coated onto the web in the form of a solution on a suspension of finely divided medicament, i.e., a collodial suspension. The liquid utilized for these operations can be water, an organic solvent, e.g., ethanol or a hydroalcoholic solvent. A preferred method of loading active ingredient in a liquid form onto a moving web is electrostatic jet spray deposition. In this method, the active ingredient containing solution or suspension is metered into an apparatus which projects a spray of microdroplets which are concentrated on a particular area of the web through the use of a defined area electrostatic field. This method has given very good results where small quantities of active ingredients such as, for example, hormones or enzymes are to be loaded on the web. By small quantities is meant active substances having a usual dosage of less than one milligram.

In addition to electrostatic jet spray deposition, certain other coating techniques recognized in other arts as being amenable to the coating of a substrate with a liquid may be utilized in loading the web with active ingredient. For example, the paper web may be passed under a roll which is immersed in a bath of saturating fluid. As the web passes the roller, the excess fluid is "wiped" from the web by another roller, a jet of air, a rubber wiping bar, a wire-wound rod, i.e., a Meier rod, or the like. In this instance there is some penetration of the web by the solution, particularly if the solvent utilized to solubilize or suspend the active ingredient is the same or similar to that utilized to form the paper web.

It will be appreciated that, while it is the object of the present invention to load the active ingredient to the surface of the web, some penetration of the web may result either from the use of a fugitive liquid carrier for the active ingredient or by the application of heat and/or pressure to the web to seal it. Simple experimentation with these factors, e.g., fugitive liquids, will determine the percentage of active substance loaded to the web which may be absorbed therein. Once this parameter is established, the on-line testing apparatus as described herein can be adjusted accordingly. Where any appreciable amount of active substance is absorbed into the web it is necessary to have unloaded web, i.e., web without active ingredient for the outer surface of the dosage unit thus preventing loss of active ingredient through exposure to deteriorating forces such as air and moisture. Obvious modifications of the fabricating processes to be described hereinafter will accomplish this result.

As stated above, one of the obvious advantages of the dosage forms of the present invention is that pharmaceutically active substance can be formulated into a stable dosage form without being admixed with conventional pharamceutical excipients which are usually present in conventional solid dosage forms in quantities far exceeding the amount of active substance. It will be appreciated, however, that small amounts of inert substances may of necessity be loaded on to the webs with the active substance in accordance with the invention as described above. For example, wherein the active substance is loaded to the web in dry foam, a small quantity, i.e., from about 0 by weight to about 10% by weight, preferably from about ¼% by weight to about 2% by weight of the active substance, of a glidant may be homogeneously admixed therewith. The purpose of the glidant is to facilitate the flow of the powdered active substance through the deposition apparatus. Suitable glidants include, for example, finely particulate siliceous preparations such as the colloidal silica marketed under the trademark Cab-O-Sil by the Cabot Corp., Boston, Mass., talc, finely particulate starch preparations, e.g., DriFlo by National Starch, Inc. and the like. It can be appreciated that the inclusion of a glidant and the quantity thereof will depend on the crystalline structure and flow properties of the active substance. In certain instances, a preservative may be admixed with the active substance. However, wherein the active substance is loaded to the web in dry form, this is usually not required. Further, it is within the scope of the present invention to admix the adhesive substances referred to above with the active substance when applying in wet form and wherein both adhesive and active substance are compatible with the same liquid carrier. In most instances, however, the adhesive substances are utilized as described above wherein the active substance is loaded to the web in dry form to enhanceadherence thereto. In either instance, said adhesive substance may be present in from 0 by weight to about 100% by weight, preferably from 0 by weight to about 30% by weight based on the weight of said medicaments.

The amount of active substance loaded to the web in accordance with the present invention will vary according to the dosage of the said substance, the area of the web to be coated, the thickness of the coating and the like. Additional factors affecting the amount of drug loaded to the web are the method of loading utilized, the parameters dictated by the fabrication process to be described hereinafter and the type and sensitivity of the on-line testing equipment utilized. In all instances, however, the amount of active substance loaded to the web is such that, when the loaded web has been fabricated and unitized, each resultant until will contain a therapeutically efficacious dosage thereof. As an example of the latter criteria, wherein the analysis of drug loading uniformity is carried out utilizing spectrophotometry employing photoncounting techniques to measure the ultraviolet absorption of the active substance of the web, the thickness of the active substance coating cannot exceed 0.005 centimeter. In any event, the amount of active substance loaded to the web is always expressed in milligrams or micrograms per square centimeter of web. This is determined for the total web surface even though in some instances it is necessary to leave a margin of uncoated web to be utilized for sealing the dosage form. The capability of the webs to receive and internalize active substance in accordance with the subject invention is expressed as the web conversion factor (WCF) and is calculated by the following formula.

$$\frac{\text{Surface area of web exposed to drug}}{\text{Maximum area of final dosage form}} = \text{Web conversion factor.}$$

For example, if web measuring 15.25 cm × 1.0 cm is exposed to drug and is fabricated to a dosage form measuring 0.5 cm by 1.0 cm then;

$$\frac{15.25 \times 1.0}{0.5 \times 1.0} = 30.5 \text{ Web conversion factor.}$$

FABRICATION

The next step in the preparation of the novel dosage forms according to the invention is the forming or fabrication step. As utilized herein, the term "fabrication" indicates transposing the web as initially formed into a solid geometric form of predetermined shape divisible into a plurality of unit dosage forms. This step may take place, as is the case with regard to the steps above-described, in a continuous manufacturing procedure at high speed. This step transforms the loaded flat web into a shaped geometric form and, generally, substantially internalizes the active ingredient within a protective coating of web. The formed web is then unitized and finished to produce pharmaceutically pleasing unit dosage forms suitable for oral ingestion. It should be noted that, in a preferred operation, unitizing would occur along with or immediately following fabrication.

In accordance with the present invention, there are several different methods of fabrication, among which can be named extrusion tubing, multiple ribbon forming, over wrapped rope forming, die forming and the like. The four principal techniques of forming or fabricating the web coated with active substance are: convolute winding, rotary forming, fan-folding and lamination. These four principal techniques are discussed in detail below.

Before discussing the individual fabrication techniques for the invention in detail, the various criteria for an acceptable technique should be reviewed. The fabrication or forming technique should be amenable to high speed manufacturing operations and produce a geometric form to exacting specifications of uniformity. The process must be capable of substantially internalizing the active substance. Finally, the fabrication or forming process must not put excessive stress on the webs so as to deform or tear them and must not dislodge a substantial quantity of active substance from the web. Each of the forming processes discussed hereinafter meet these criteria.

The first principal technique to be discussed concerns convolute winding of a moving web. It is perhaps appropriate to distinguish between convolute winding and spiral winding as recognized, for example, in the paper-converting industry. In spiral winding, the paper is fed to the spiral winding machine from several rolls where it is usually in coils that are ½ cm to 2 cm wide. The continuous strips of paper from each roll are coiled around a cylindrical mandrel which is supported at one end. The strips are coiled in such a way that they overlap. An adhesive is applied to each strip of paper and the overlapping strips from a continuous spiral as they are wound around the mandrel. The roll thus-formed is caused to rotate about the mandrel by the action of a continuous belt which also forces the paper roll forward toward the unsupported end of the mandrel. At the end of the mandrel, the tube thus-formed is cut into desired lengths by the intermittent action of a high-speed knife. Paper which is converted in this way would always have a hole in the middle by virtue of the mandrel upon which it is formed. In the convolute-winding process, there is no mandrel, and, therefore, it is not necessary nor desirable to have a hole in the center of the formed rod. In fact, it is expressly intended by this invention to severely limit or eliminate altogether this central hollow area.

Figure 3:
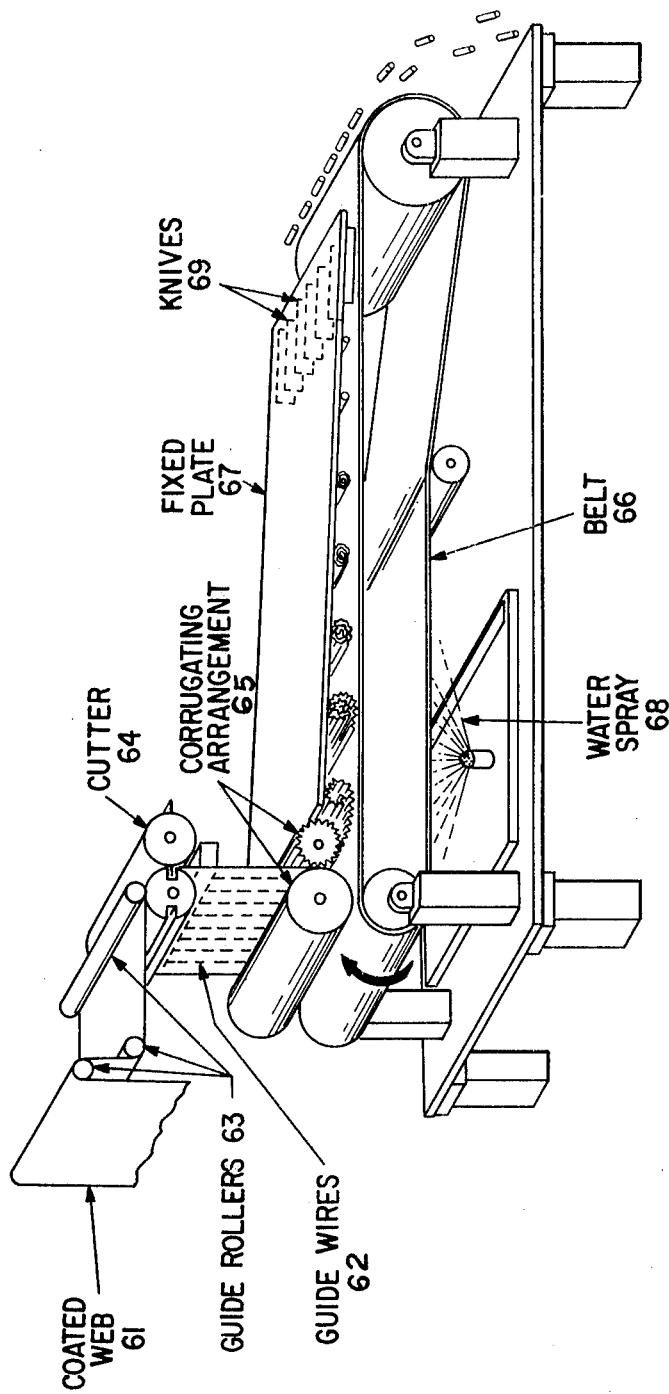
FIG. 3 is a diagrammatic representation of an arrangement for carrying out the convolute winding technique of dosage form fabrication.

Reference is made to FIG. 3 which diagrammatically illustrates one example of convolute winding. In the convolute winding process of FIG. 3, the coated or loaded web 61 is fed from a single roll through a system comprising, for example, guide wires 62 and roller 63 to a cutter arrangement 64 which cuts the web transversely into desired lengths, usually from about 12 cm to 25 cm in length. The sections of web are then guided into a corrugating roller arrangement 65 wherein a corrugating roller forms a series of creases by pushing the web against a soft rubber roller. As a result of the corrugating action, the individual sections of web are formed or curled into loosely wound coils. The loosely curled webs emerging from the corrugating roller arrangement are then passed between a stationary surface and a moving surface, wherein the space between the two surfaces is gradually decreased along the course of travel of the curled webs. The stationary and moving surfaces may be in the form of two concentric cylinders, wherein one is stationary and the other rotates relative to the stationary cylinder, or, as shown in FIG. 2 they may be in the form of a flat fixed plate 67 as the stationary surface and a moving belt 66 as the non-stationary surface. As the sections of web as loosely wound rods pass between the moving and stationary surfaces, they are wound tightly until a firm rod is formed. By appropriate adjustment of the spacing between the two surfaces, the rod can be wound tightly enough to eliminate any hole in the middle. It will, of course, be appreciated that, if desired, the spacing can be made so that a hole of desired size is left in the middle of the formed rod.

The rod can be sealed by several methods. First, it has been found that the conventional process of making, e.g., confectionary sticks is unacceptable in the practice of the present invention. In the conventional method the moving surfaces that come in contact with the web during rod formation are sprayed or coated with water to contact a large portion of the web. The amount of water absorbed by the web, about 18% by weight, is unacceptable for the preparation of the unit dosage forms of the invention due to possible deleterious effect on the adhesion of the medicament to the web as well as on the medicament itself. Further, the rods formed by this conventional process have been found for the most part to be too sealed to give a good release of medicament in the body. It has been discovered in accordance with the present invention that spraying approximately the same portions of the web as in the conventional process with a sufficient amount of a fine spray of water to merely dampen it and rapidly drying the rods after formation yields final dosage forms possessing acceptable uniformity and rate of release of medicament as well as stability in terms of the active ingredient with the obvious exception of those medicaments which are recognized in the art of pharmaceutical compounding as being highly sensitive to the presence of moisture.

Second, the rods may be sealed by the application of a piece of heat-sealable edible polymer to the trailing edge of each sheet of web or the trailing edge of each sheet is coated with a heat-sealable, edible polymer directly after the cut is made from the endless web. Alternately, a heat-sealable polymer may be applied over the entire section of web either as a separate sheet or as a uniform coating. Suitable polymeric material would include, for example, a water-soluble polyoxyethylene or cellulose ether derivative containing a plasticizer such as is described above. After the rods are tightly wound, they are in such an instance made to pass under a heated plate where both heat and pressure are applied to effect a seal. For example, a portion of fixed plate 67 could contain a heated section.

Alternately, the rods, after formation, may be sealed by the application of water or an adhesive to the outer layer(s) or web. Preferably, water is used as the sealing agent. This method would likely require the presence of substances in or on the web composition, for example, starches or starch derivatives, which would form a seal through subsequent drying or with the application of heat and pressure.

The method illustrated in FIG. 3, for purposes of example, provides for a water spray 68 to contact the outer surface of the endless belt 66 along to lower, return portion thereof, such that the belt surface contacted by the rolled web sections retains only enough water, droplets to effect a proper seal of the rods. The water could also be applied to the tightly wound rods, for example by passing them under a water transfer roller, a porous plate through which a metered quantity of water is uniformly applied to the total length of the rods, or a sponge arranged to apply water to the outer surfaces of the rods. The rods could then be caused to pass between a further section of the moving and stationary surfaces where pressure or pressure and heat may be applied to effect the completed seal.

This general method of effecting a water seal is deemed clearly superior to known methods of forming, for example, confectionery sticks as described above. With the water application methods as above-described the total amount of water applied to each rod is less than that applied by known methods. As a result, the amount of water to be removed during subsequent drying of the rods is substantially less than that generally required with known methods.

The rods thus-formed are each as long as the width of the web of the supply roll. This width is typically 20 to 40 cm. After each rod is sealed, it is caused to move into contact with, for example, ultrasharp knives 69 (FIG. 3) via the belt 66 where it is unitized, i.e., the rod is cut to desired lengths. Methods for unitizing and finishing these rods to final dosage forms are discussed below in further detail.

Figure 4:
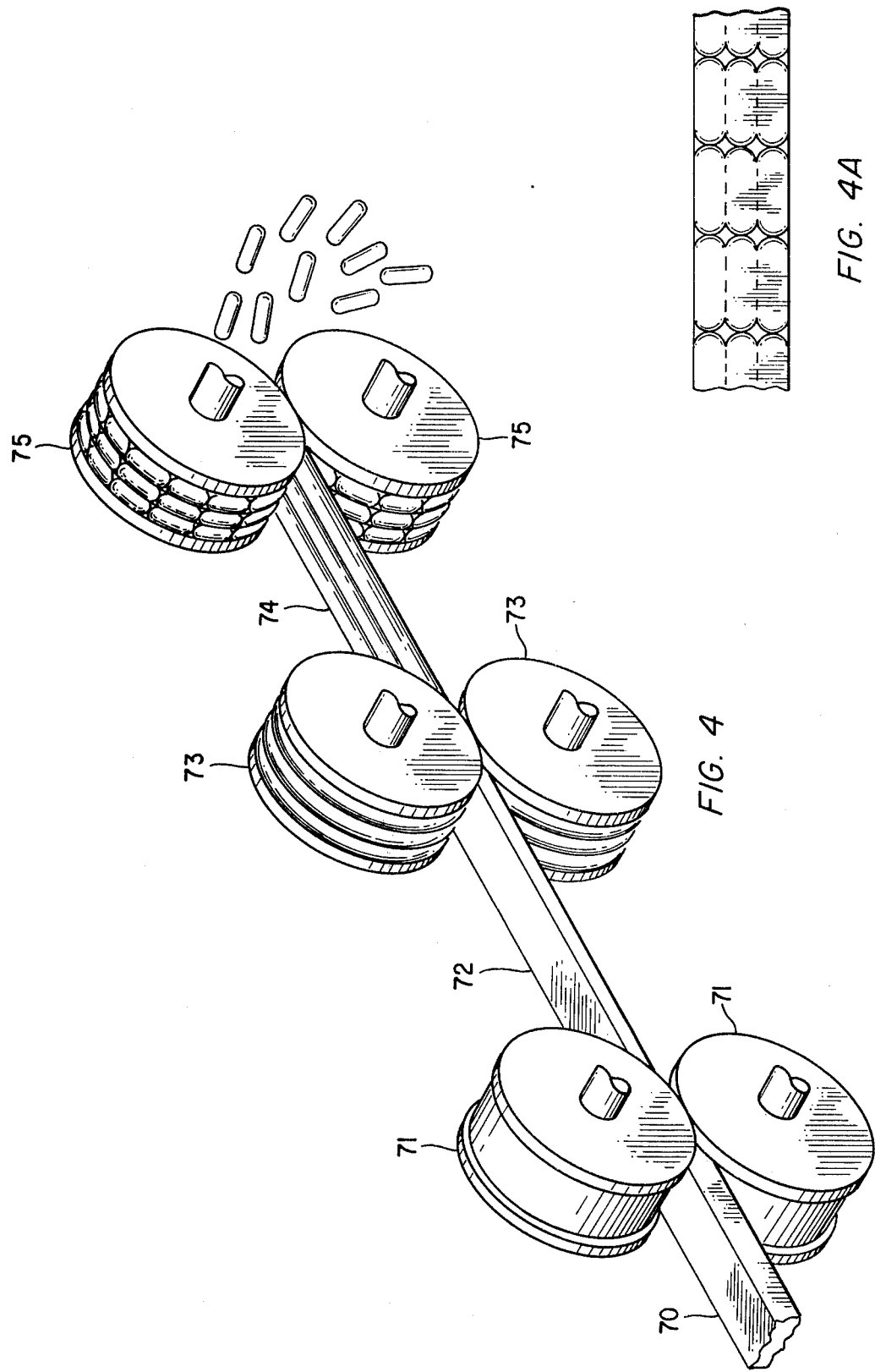

A second forming or fabrication method to be considered is generally identified as rotary forming. This method can take several specific forms. This method may be considered as being related to the more generic lamination method in that, in this method, stacks of web loaded with active substance in endless strip or rod arrangements are initially prepared either by fan-folding of lamination, both of which are discussed hereinafter. In one specific rotary forming method, as illustrated in FIG. 4, a continuous, relatively thick strap of stacked webs of web 70 loaded with active substance is passed between a pair of press rollers 71. The continuous thusly formed or pressed laminated stack 72 is fed to a second station, i.e., a rod shaping and densifying station, comprising, for example, one or more spring loaded stainless steel rollers 73 having a circumferential edge shaped to transform the strap into a plurality of continuous rods 74, or largely circular or other desired cross-section. The rods 74 shaped thereby into desired geometric form are then passed through a third rotary station where, for example, one or more pairs of suitably arranged rollers unitizes the rods into individual doses. This may be followed by other suitable printing and finishing operations as are more particularly described hereinafter. It should be noted that the printing operation could be carried out in the unitizing step involving the third set of rollers 75.

Figure 5:
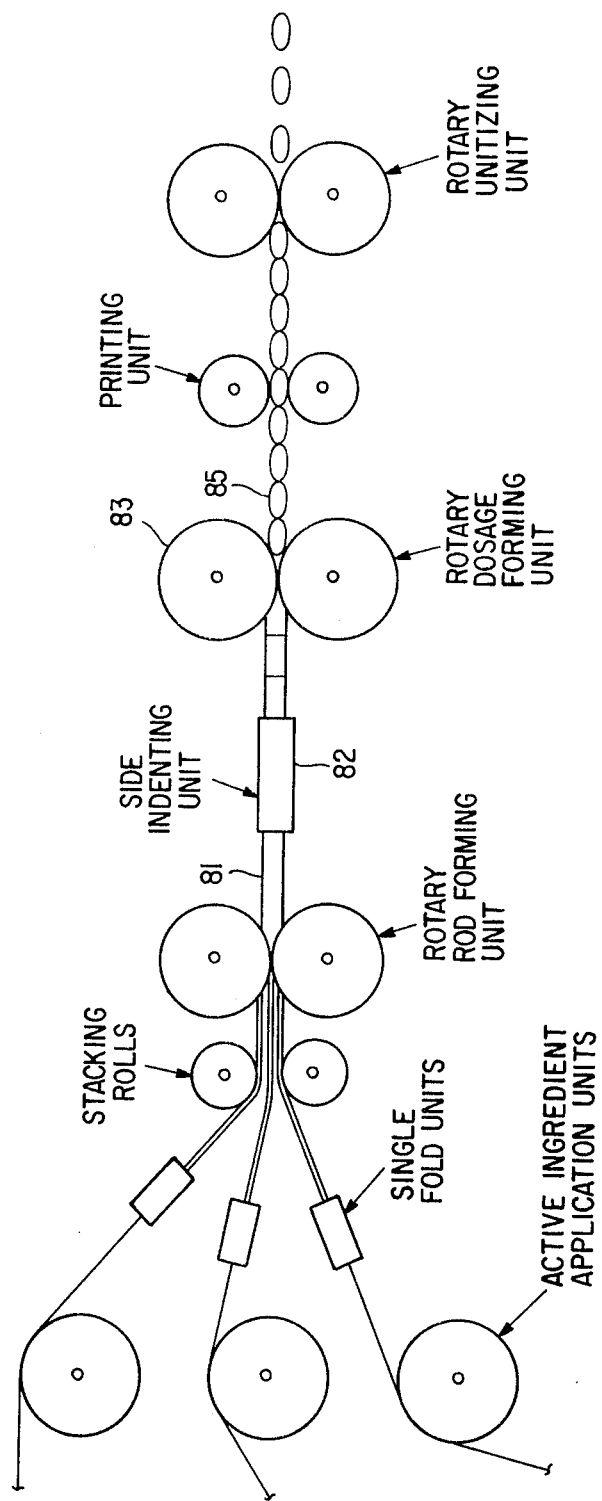

Another example of rotary forming is shown in FIG. 5 wherein the formed endless stack (strip or rod) 81 is continuously indented at regular intervals by reciprocating die blocks 82 and/or a pair of suitable heated rollers 83 to provide ultimately rounded corners in the final dosage units, such that the output of the rotary dosage forming station is a continuous chain of end-connected dosage units 85. As with all or the various methods of rotary forming according to the invention, the thusly altered rods are passed through printing and unitizing stations or subassemblies, all at high-speed.

In another closely related rotary forming technique, the continuous stack is fed into a rotary shaping and densifying assembly comprised as before of, for example, one or more pairs of stainless steel rollers. The layers of web, which may be made from layers of paper and polymer film, are heated and compressed into a continuous stack. It is preferable that the outer layers of the stack be paper, for example, to prevent sticking of the stack assembly to the heated rolls. During this densifying operation, the layers of web are bounded together as a unit which reduces shifting of the layers and splitting of the edges during subsequent side- and end-forming operations. Next, the ends of the dosage units are formed by feeding the continuous rectangular stack produced at the densifying station into a second station where the ends of the dosage units are formed by a pair of heated rollers which may have shaped, transversely-oriented cutters located on the rollers faces. The cut ends of the dosage units are shaped and sealed by the heat from the rolls. The configuration of the end cutter determines the shape of the ends of the dosage units. The shape of the end cuts is designed to provide a smooth transition with the side cuts of the dosage units which are performed in the next station.

The sides of the dosage units are formed in the laminated end-formed, cut material stack with a third pair of heated rolls. These rolls may have angular grooves with raised cutting edges. The configuration of the grooves in the roll faces forms a desired dosage unit cross-section. Heat and pressure applied from the ridge-like cutting elements on the rolls seals the sides of the dosage units into a smooth surface.

The rotary-forming method of dosage unit fabrication illustrated in FIG. 5 consists, therefore, of three primary stations, viz. a pre-densification station, an end-forming station, and a side-forming station. Each of these stations consists of a set of rollers, preferably heated, through which the continuous web stack is passed. The configuration of the outside surface, i.e., the face of the rollers at each of the stations is different, depending on the particular station and the result to be accomplished. Various additional operations, such as additional cutting, printing, or finishing steps can be performed between or at the three stations described. These operations are described further below.

It is to be noted that it is within the scope of this invention to provide one or more of the various steps in the rotary forming method simultaneously, and, in fact, perform on the endless laminate input strap, via a single pair of, for example, spring-loaded, heated cooperating rollers, all of the various above-discussed steps, i.e, rod-forming, dosage-forming, unitizing and even printing.

The above-described third example of rotary forming readily lends itself to an example of combining two or more of the outlined steps into one. Such is illustrated in FIG. 4A wherein essentially the laminating press and rod-forming steps of the above-discussed third rotary forming method and also the method as illustrated in FIG. 4 are combined, for example, through the use of a single pair of heated, pressing and cutting rollers (not particularly shown) which simultaneously press the laminate feed and end cut it into a shape resembling a side view of a plurality of stacked doughnuts. These end cut sections are then immediately fed to a unitizer which provides the longitudinal cuts enabling the individual dosages to be realized. The printing step, for example, could also be performed at this latter station. It is also within the concept of the present invention to package the unitized dosage forms directly as they come from the unitizing operation, for example, by inserting them into blister strips by apparatus considered conventional in the art.

A third method of forming dosage forms in accordance with the present invention is the fan-folding technique. One could also classify the fan-folding technique as being a form of lamination in a general sense. In this method, a web up to, for example, 30 cm wide is first fabricated to internalize the active ingredient loaded thereon. This may be accomplished either by initially folding the web in half or by laminating two coated webs with the coated surfaces facing. A stack of more than one pair of webs laminated in this manner may be utilized, the webs may initially be formed, for example, to a greater width, i.e., up to 60 cm and, following lamination, divided to form two or more widths of a size described for the fan-folding operation, i.e. from about 1 cm to about 15 cm After the coated web has been initially folded or laminated as described above, it is then passed through scoring rolls where it is scored in preparation for the fan-folding operation. The scoring rolls may or may not be powered. The web is basically moved by pulling rolls. Scoring can be accomplished, for example, by spring-loading one of the pair of scoring rolls. Since the web folds preferentially in the direction of the score rings which impress into the web material, the score rings may be positioned alternately in the upper and lower rolls in accordance with the desired fan-fold pattern. The scored web then passes into a fan-folding chute having folding blades which begin to gently bend the web at point of contact and constrict both in width and overlap so that the web is reasonably tightly folded at the discharge end. At the end of the fold chute is a means for pulling the web through the scoring and folding apparatus such as, for example, a pair of stainless steel, spring-loaded driven rollers. This serves a dual function, i.e., the web is moved through the folding apparatus and the folded web is compacted into a continuous, solid geometric form. It is, of course, within the scope of this invention to combine the pulling means with means for sealing the web. However, the fan-folded web may be sealed by other methods as will be described hereinafter. The sealed webs may be unitized in a number of ways such as the rotary forming method described above.

Figure 6A:
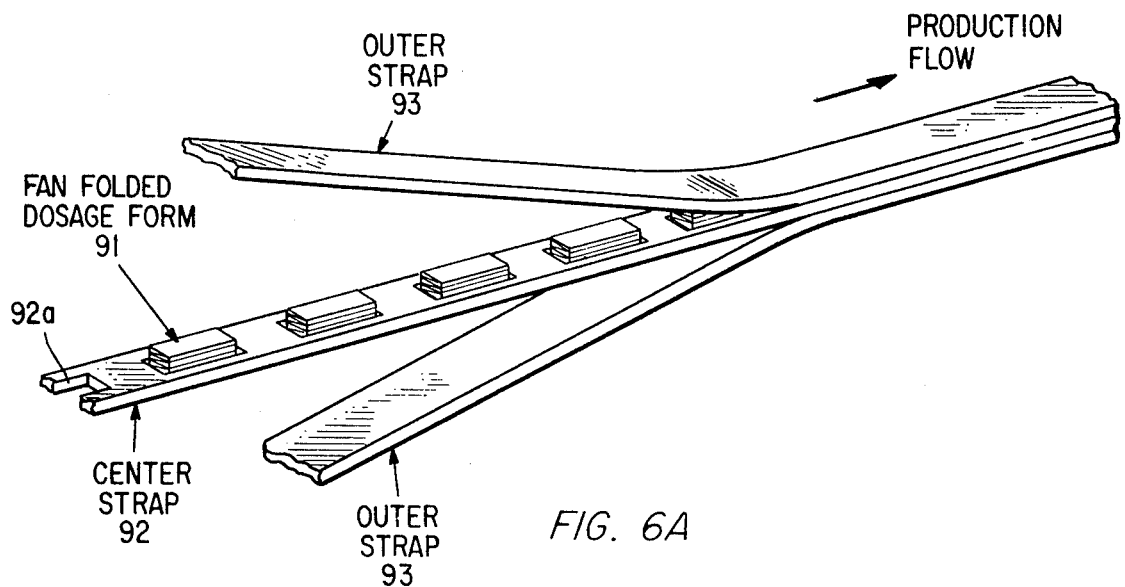
FIGS. 6A–6D illustrate the finishing and sealing aspects of the fan-folding technique of dosage form fabrication.
Figure 6B:
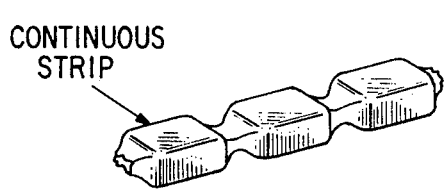
Figure 6C:
Figure 6D:
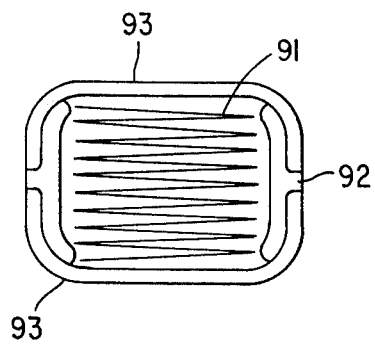

In FIGS. 6A–6D one fan-folded dosage form technique is illustrated wherein the initial fan-folded webs 91 are assembled in perforations 92A of cooperating shape in a therapeutically inert web structure, preferably comprised of paper, identified as center strap 92. This "loaded" center strap bearing the fan-folded webs is then sandwiched between outer straps of web 93 to form a composite laminated structure. This composite endless laminated strap is then fed to, for example, a rotary dosage forming unit or station not unlike that of unit 83 of FIG. 5, wherein the strap is caused to take on the appearance of that shown in FIG. 6B. Finally, or simultaneously with the step performed in relation to FIG. 6B, the unitizing step is performed, rendering individual dosages such as illustrated in FIG. 6C. FIG. 6D illustrates in cross section the dosage form illustrated in FIG. 6C. FIG. 6D shows how the fan-folded webs 91 are completely internalized and that, e.g., the center strap 92 is forced by the molding process outwardly somewhat so that some of it is exposed between the edges of outer straps 93 which are sealed thereto. It should be noted that, preferably, outer straps 93 and center strap 92 are free of any active ingredient thereby ensuring that none of the active ingredient will be present on any exterior surface of the individual dosage forms.

The fourth principal forming method contemplated by this invention is the lamination method generally alluded to hereinbefore. In this method, between about 20 and 60 rolls of web are first simultaneously unwound from a multiple-reel unwind stand and then guided together to form a continuous rod. The 20 to 60 layers of web may all be paper-like material with an appropriate coating to facilitate sealing in a subsequent step, or they may be a laminate of a paper-like web and a heat-sealable, edible polymer web, or they may consist of one or more paper-like webs alternately interspersed with heat-sealable, edible polymer webs. Suitable polymeric materials include, for example, a water-soluble polyoxyethylene or cellulose ether derivative containing a plasticizer. Any number of the webs may be loaded with active substance. Preferably the paper composition webs are loaded with active substance.

An alternate method for stacking the webs which are loaded with active ingredient is to supply them directly from the deposition apparatus. The width of the web is usually 12 to 25 cm. The web, as stored on rolls or supplied from the deposition apparatus, may initially be multiple of the final width which is slit to the final desired width as part of the stacking process.

Once the web is stacked, the continuous resultant bundle is guided to a lamination station. Apparatus known in diverse arts for bringing strips of flexible films together and forming a laminate therefrom is generally applicable to the practice of this embodiment of the present invention. As already discussed, the area of deposition of active substance on the web strips or sheets will vary depending, for example, on the method of sealing the lamination. The cutting and finishing of the laminate may likewise vary in accordance with the invention. For example, laminates can be treated as in the rotary forming process described above. However, the lamination station could also consist of a pair of reciprocating die plates which form, seal, and cut dosage forms from the continuously feeding web stack. A typical die plate would have a surface of approximately 25 cm × 25 cm.

The laminates formed in accordance with the present invention are, in a particular embodiment, unique in that they are sealed only at the edges as opposed to each sheet being totally sealed to the adjacent sheets. It has been found that, unexpectedly, suitable dosage forms can be produced from a stack of layers of web wherein up to six layers of paper composition web are interspersed between layers of a web comprised of a heat sealable polymeric composition by the application of heat and pressure to the stack by the cutting means during unitizing. During the unitizing operation, the layers of polymeric web in the stack become distorted by the heat and pressure and "spread" to cover and seal the edges of the intervening layers of paper composition. It is readily apparent that the top and bottom layers of such a laminate must be of polymeric composition. It is preferred that the medicament in a paper-polymeric web stack be loaded to the paper layers of web. It is readily apparent from the foregoing disclosure that such a laminate sealed only at the periphery possesses a superior rate of release of medicament than a similar stack of webs which has been totally laminated.

An alternative method for forming the dosages from the web stack is to pass the stack between rotating cylinders which have individual dual dies on the outer periphery. The dosage units are formed, sealed and cut from the continuously feeding web stack as it passes between such rotating cylinders.

Some pharmaceutical compounding benefits are realized from the use of laminating techniques are herein considered. First, the laminating techniques provides barriers which facilitate the compounding of two or more therapeutically active substances which are incompatible without the need to resort to the addition of stabilizing substances or a special compounding technique such as, for example, encapsulation of one or more ingredients. Since up to, for example, 60 layers may be utilized to form a laminate, this embodiment of the invention is ideally suited for pharmaceutical preparations containing a large number of active substances where there are numerous possibilities of incompatibilities such as, for example, multivitamin preparations. Further, the insulating effect of layers of a laminate and the deposition or loading of active substance to the web in the dry state makes such techniques ideally suitable for the dispensing of effervescent preparations. In such preparations, it is appreciated that the web composition would have to be such that it would readily dissolve or disperse in water. Also, as discussed above, loading of the active ingredient onto the web in the dry state is advantageous wherein the active substance is adversely affected by moisture.

Further regarding the laminate process of the present invention, it is within the scope thereof to vary the formulation of the various layers within a laminate as well as to control whether each is coated with active substance. Obviously, the surface of the top and bottom layers of a laminate which will be exposed is not coated thus providing effective internalizing of the active substance. For, example, it has been found that interspersing one or more layers of a starch-based formulation in a cellulosic laminate more expediently adds plasticity to the laminate than increasing the quantity of plasticizer in the formulation of the cellulose layers.

Regarding the method of forming discussed above, it is preferred in accordance with the invention to deposit or load the web with active ingredient in the wet form wherein forming is by the convolute wind or fanfold process. The rotary forming and lamination processes are equally amenable to deposition of active substance in wet or dry form with the choice being dependent on the characteristics of active ingredient being loaded, for example, solubility in the particular solvent being utilized, stability to moisture, and the like.

UNITIZING

As a practical matter, unitizing cannot be discussed without also discussing sealing, and without first having discussed fabrication, since, by definition, cutting or unitizing the formed webs could expose some active ingredient at one or more of the outer surfaces. An exception to this would be having the loading operation adapted to deposit active substance at short intervals as opposed to a continuous deposition thereby having active substance "spot deposited" and surrounded on all sides by uncoated web. In view of considerations of manufacturing equipment and the need to maintain the integrity of the deposition coating for on-line testing, it is preferred to load active substance continuously onto the web in sufficient amount so that the unitizing operation produces dosage forms containing a therapeutically efficacious dosage. In certain of the operations described herein, e.g., the fan-folding process, the outer margins of the web may be left free of active substance to insure internalizing of the active substance and, in certain instances to provide excess web which can be utilized to seal the unitized dosage forms.

The cutting of the formed web must be accomplished in such a manner so as not to deform the web. The cutting operation itself may be accomplished by stationary or rotary knife blades, by single- or two-stage dies, or by other conventional methods. To assure that the fabricated web will not be deformed during the cutting operation, several cuts may be made from different angles. Also, as discussed above with regard to rotary forming, the formed web can initially be crimped slightly or indented to compensate for the distortion caused by the high speed unitizing operation.

The formed, loaded web may be unitized by individual separation, i.e., the formation of one unit at a time such as by cutting exact lengths from a rod or, preferably, a number of units may be formed simultaneously such as by cutting a convolute wound rod into a number of dosage units utilizing a number of uniformly spaced cutting edges. Another method of forming a plurality of dosage units simultaneously would be the use of shaped dies, either single or double and rotary mounted, or reciprocally mounted on plates to cut a laminated web or a convolute wound rod-like structure. The shape of the final dosage form preferably has cosmetic appeal and is such that a number of shapes will fit into a die plate with essentially no waste except at the periphery a rectangle, a square or, preferably, a hexagon.

The shape of the dosage forms prepared from rods can also be determined by the shape of the cutters. The cutter, for example, could be of rectangular shape with the parallel larger sides moderately concaved so that the ends of the dosage forms cut therewith will be slightly rounded. Other variations will be apparent to those skilled in the art. It is to be borne in mind, however, that such lateral support as is required to prevent wrinkling and flashing must be applied to the fabricated dosage forms during the unitizing operation.

It is within the scope of the present invention to combine the unitizing and final sealing operations. Although there are numerous ways by which the dosage forms can be sealed, the most commonly combined with the unitizing operation are heat and/or pressure. In addition to effecting a seal on the severed edges of the dosage form by heating the cutting tool, heat and pressure can be applied through the die to bond the laminate. Also, the use of moisture or a fugitive solvent to seal the trailing edge of the convolute wound rod as mentioned above can be extended to the cutting operation by applying such solvent to the cutting surface. Heat and/or pressure may also be applied at the same time to ensure a proper seal.

The methods whereby the unitizing dosage forms prepared in accordance with the present invention may be sealed are not unconventional to the plastics handling and laminating arts. These include, in addition to the use of water or other fugitive solvents such as, for example, ethanol, methanol and chloroform, the application of pressure and heat, the application of a separate adhesive, infrared heating, ultrasonic bonding, encapsulating or combinations of two or more of these. A preferred method of sealing dosage forms within the scope of the present invention is the use of an overwrap which may be preprinted if desired. This may be, for example, a thin layer of edible polymeric material such as, hydroxymethyl cellulose, modified starch, and gelatin which is sprayed on to the dosage units of a bath into which the dosage units are immersed. Such layer could be self sealing such as, for example, by removal of a fugitive solvent. More preferred methods of effecting a sealing layer on the unitized dosage units in accordance with the invention are encapsulation and basket sealing.

In the first of these methods, the solid dosage units are passed between converging layers of flexible film of, for example, gelatin which enclose the dosage form such as that illustrated in FIG. 6A. The gelatin film is then heat sealed and cut to shape. Apparatus for encapsulation of liquids by this method is recognized in the pharmaceutical industry and such apparatus can readily be adapted to coat the novel dosage forms of the present invention.

A second method is basket sealing which may be accomplished by at least the following two processes. In the first, preformed baskets are prepared from material such as, for example, gelatin, or a cellulose derivative by apparatus well known, e.g., in the art of plastic molding, i.e., injection molding. The unitized dosage forms are placed automatically into these baskets at high speed and the baskets are then covered by an overlayer which is sealed to the basket by any of the sealing methods alluded to herein, preferably ultrasonic welding. The baskets are separated by cutting with a stationary or rotary cutting edge. The walls or the preformed basket are usually thicker than the top or sealing layer. The sealing layer, however, is sufficiently thick to protect the dosage form yet is such that the dosage form will be released from the basket via the sealing layer within a very short time after ingestion, usually within a few seconds after reaching the stomach. Alternately, the basket may be formed from identical halves which are sealed by methods such as have been described herein.

An alternative to the basket seal described above is to form a continuous support web or strap of material such as described above for the basket and cut holes therein to exactly accomodate the dosage form, e.g. fan-folded dosage forms as illustrated in FIG. 6A. In this embodiment, the unitized dosage forms are placed into the holes, e.g., by a pin through the hole and a second pin on top of the unitized dosage form to keep it under compression. The strap is then sealed by the addition of a top and bottom layer of similar material while maintaining compression on the dosage units. The thickness of the strap is in no instance more than that of the dosage units. The strap, however, can be thinner than the dosage form but not less than approximately half the thickness thereof. It is preferred that the support strap be close to or equal to the thickness of the dosage form for a number of reasons. First, the sealing film can be as thin as that described above in connection with the basket since it is not significantly distorted in the sealing operation. Second, a thicker support web will be less subject to distortion during the perforating and unitizing operations. Third, holes can be made closer together in a thicker strap thus allowing for a minimum of waste. Once the dosage form has been placed in the support strap and sealed, the strap is again unitized as described herein. An advantage to both the basket and support strap concept described above is that there is web material on the outer surface which does not contain active substance and which could be subjected to finishing operations such as, for example, embossing, beveling, and the like without risk of loss of active substance. Also, the use of the basket or the support strap concepts facilitate the use of varying colors in the final dosage form, e.g., by making the support web, sealing strips or the dosage units themselves contrasting colors, an especially pleasing and distinctive appearance may be achieved.

The material to be utilized in preparing the basket, center support strap and sealing films described above must, as is the case with the webs themselves, meet critical tests. In addition to the obvious pharmaceutical criteria of purity, having good shelf life, being non-toxic and compatible with the active substance utilized, the material must have good surface quality, color and ink receptivity, structural integrity, deformability, dimensional stability and release of active ingredient in water. The preferred substances for this use are hydroxypropylcellulose and methylcellulose. An especially preferred composition comprises hydroxypropylcellulose, a starch or starch derivative as an extender and disintegrant, a plasticizer such as, for example, polyethylene glycol, suitable pigments, e.g., titanium dioxide and an antioxidant such as, for example, BHT.

QUALITY ASSURANCE

One of the major advantages realized by the novel dosage forms of the subject invention is that they are amenable to on-line, non-destructive quality assurance. In the context of the present invention the term "non-destructive" is meant in the practical sense as opposed to the strict literal definition. By this is meant that quality assurance of the novel dosage forms of the invention is provided duuring high-speed manufacturing procedures with the actual loss of substantially less than 1% of the dosage form. Since the novel dosage forms of the invention can be produced with a low standard deviation in dosage and therefore a manufacturing excess of less than the standards conventionally accepted in the pharmaceutical industry at the present time, the very small percent of the dosage form lost during testing becomes in essence, zero when viewing the tolerances of the instant manufacturing process in total.

The novel dosage forms of the present invention, as a finished product, possess quality assurance of the manufacturing process, a concept unique in the pharmaceutical industry. The on-line testing procedures giving such assurance are to be clearly distinguished from such recognized pharmaceutical quality control procedures as chemical and physical control of the ingredients of the dosage form before the manufacturing has begun, destructive testing of solid dosage forms after the manufacturing procedure has been completed both for physical characteristics, e.g., dissolution rates, incidence of capping and the like and chemical characteristics such as potency, presence of incompatibilities and the like and physical quality checks of solid dosage forms such as, for example, manual inspection of bicolored capsules to assure that each has ends with contrasting colors. Such tests, which are recognized and commonly practiced in the pharmaceutical industry and described in the official compendia, bear no relation to and are not suggestive of the on-line manufacturing assurance which is a critical feature of the solid dosage forms of the invention. It is to be noted, however, that certain procedures such as, for example, strict quality control and testing of all ingredients prior to the manufacturing process form an integral part of the preparation of the dosage forms contemplated herein as is the case with any good pharmaceutical manufacturing practice.

The on-line quality assurance of manufacturing possessed by the novel dosage forms of the present invention is provided by the fact that all such forms described herein begin with a continuous edible web which can be tailored to non-destructive testing. First, the web production itself is monitored for the physical characteristics of the web to assure that the web is uniform and is free of defects. For example, the web can be made to pass through a resonant cavity where a microwave passing through the web is continuously monitored for web thickness, i.e., once the resonant frequency is established, changes therein are indicative of changes in web thickness. Other means of monitoring web thickness include laser beam diffraction, fluidic sensing and physical contact sensors. It is also possible in accordance with the present invention to test the web for weight per unit area and for defects.

The preferred method of testing the web for weight per unit area is soft x-ray absorption, e.g., a wavelength of about 4 angstroms. Beta-ray absoption unitizing a PM 147 source is also feasible. Web defects such as specks, holes and streaks can be detected by laser beam scanning. Holes in the web can be detected by the electrical discharge method utilizing equipment which is commercially available.

The methods detailed above are equally applicable in those instances where the web receives a second coating either in the form of one or a number of additional webs or a protective coating applied to a loaded web. Laser scanning is particularly advantageous to the on-line quality assurance of such coatings.

A second major area of quality on-line assurance in accordance with the method of the present invention is monitoring of the amount of active substance deposited onto the web and also the uniformity of the coating operation. It must initially be remembered that a distinct advantage of the process by which the novel dosage forms of the present invention are produced is that the active substance is loaded to the web in a form which is amenable to the testing procedures to be described hereinafter, i.e. in finely particulate form or as a fine film.

There are several methods contemplated herein for analysis of uniformity of deposition of active substance. For example, a photon counter can be utilized to measure ultraviolet absorption of the highly attenuating active substance-web system. Soft x-ray absorption utilizing a wavelength of about four Angstroms and beta-ray absorption can also be utilized. Light scattering apparatus is preferred since it is ideally suited for monitoring particle size and concentration in the powder cloud or on the web. The apparatus suitable for such operations is commercially available.

The fabrication, unitizing and finishing steps described above are likewise amenable to on-line testing procedures such as described above in connection with the web. Such tests will, of course, involve physical parameters of the web after fabrication such as dimensions, thickness, uniformity and the like. Similar tests are also carried out on the unitized dosage forms regarding shape, uniformity and the like.

The discussion to this point has centered on means whereby the novel dosage units of the invention are tested non-destructively on-line during production. Two additional tests are contemplated within the scope of the invention and without departing from the spirit of the terminology "nondestructive testing".

In the first such operation, a minute portion of the web is periodically removed on-line by cutting with knives, dies, fluid jets or a laser beam. It is comtemplated that the portion of web removed will not destroy the integrity of the web or adversely affect any of the fabrication operations. The sample of the web can be removed before or after the active substance is loaded thereon or, in some instances, during early stages of fabrication, e.g., when few webs hve been stacked in a preliminary laminating or folding operation. The sample thus removed is chemically analyzed both for web composition and for active substance. This analysis is also carried out on a quantitative basis particularly with reference to active substance.

In addition to the spot analysis, the finished dosage forms are sampled and subjected to performance assurance on-line. While such testing is a procedure required at present with most solid dosage forms marketed in the United States it is not carried out on-line during the manufacturing operation as is the case with the present invention. First, it must be borne in mind that the novel dosage forms of the present invention are not encumbered by batch restrictions by virtue of the process whereby they are manufactured. A "batch" in accordance with the invention can therefore be the number of dosage units falling between two samples which meet the performance specifications provided that said number does not exceed the sampling requirements of the Federal Food and Drug Administration. Since the sampling procedures contemplated in accordance with the invention substantially exceed such requirements, a batch of novel dosage units claimed herein can be any convenient number, e.g., the number of units which can be produced from a given production lot of active substance.

A second unique aspect of the performance assurance testing of the novel dosage forms of the subject invention is that the results of such tests, as well of those of all other on-line tests discussed herein, can be computerized and utilized to adjust the parameters of the manufacturing process. By so doing, a negative reading on any of the tests signifies the beginning of a run of dosage units which must be isolated and the next following positive result after corrections are made automatically terminates the run. The dosage units produced between these two tests must then be further tested to determine how many conform to specifications. Where tests are being conducted on-line on the web, e.g., on the amount of active substance deposited, a negative reading can be automated to simultaneously actuate two functions. First, the web can be marked with a spot of non-toxic dye thus allowing for the production procedure to be temporarily halted and a section of web manually removed. Second, the reading, through a computer, actuates an adjustment in the amount of active substance being loaded onto the web to either increase or decrease said amount to conform to specifications. When the web passing the testing unit again conforms to specifications, a second spot will automatically be made on the web thus marking the length of web not meeting specifications. Similar operations are established at each of the on-line test sites.

Regarding the performance analysis operation, random samples of finished dosage units are removed and automatically deposited in aliquots of test solution and tested for dissolution rate. The particular criteria utilized to test for dissolution of the unit dosage forms will vary with the active substance or substances present therein. For example, a sample dosage unit can be added to a suitable solvent thereby forming a solution of the active ingredient. The resulting test solution can be photometrically scanned to record the concentration of active ingredient as a function of time after the test unit was inserted therein. Other possible indicators which could be measured in the test solution are changes in pH, color, heat, chemical reaction and the like. Means whereby each of these changes can be automatically recorded as a function of time are within the skill of the art. Once the dissolution information is recorded, it can be utilized by a system such as a computer to make such adjustments in the formation, unitizing, finishing and sealing operations as are required to correct or improve the readings.

The on-line testing procedures described herein are in all instances amenable to testing of the entire web, e.g., a device which tests for web thickness. However, in certain instances testing of the entire web may not be feasible from the standpoint of economics. For example, it is possible to test a small area of web using a light scattering sensor and further possible to mount two or more sensing devices in close proximity to scan a corresponding number of small widths within a passing web. The cost of equipment required to have the total web scanned may, however, be prohibitive. Therefore, where only limited areas of the web can be checked, the testing equipment can be mounted on means which facilitate its oscillating across the width of the web. The percentage of web and therefore finished dosage units tested in this manner far exceeds any nondestructive testing procedures presently carried out in the pharmaceutical industry.

FINISHING AND PRINTING

As discussed at various points herein, the finishing operations for the novel dosage forms of the present invention may be conducted independently or, preferably, in combination with other operations, e.g., unitizing. finishing in terms of the novel dosage forms of the present invention is divisible into two basic considerations, i.e., the uniformity of the surface of the dosage form and the finish or appearance of the surface thereof.

Uniformity of surface of the dosage forms of the invention may or may not be a problem depending on the technique employed to unitize the dosage forms from the continuous stack and whether a sealing operation is performed. For example, wherein a laminated stack of webs is cut to a particular shape as described above, a small flashing may be evident where the cutting means meet. Also, there may be some end or side flashing from the unitizing operation in dosage forms formed by other preferred methods of fabrication. Generally, however, the fabrication techniques of the present invention minimize the incidence of such flashing.

Flashing as described herein is generally removable by mild abrasion such as, for example, by subjecting the dosage units to mild tumbling action with or without the presence of a mild abrasive substance such as salt crystals. It is realized that such action must, in most instances, precede printing operations.

The surface appearance, i.e., the gloss of the dosage forms of the present invention may vary from a mildly buffed appearance to reasonably high gloss depending on the technique utilized and the finish desired. Wherein sealing techniques such as, for example, the basket sealing or encapsulation methods referred to above are utilized, the gloss of the finished surface can be adjusted as desired by merely the selection of material utilized in forming the seal. The same is true wherein an overwrap is utilized to seal the dosage forms. Wherein such sealing operations are employed, complete removal of the flashing is usually not required since the overwrap assures complete continuity of surface.

The printing operation is likewise dependent on the fabrication and sealing techniques utilized. Printing may be effected on the web itself at any convenient point in the overall manufacturing operation. For example, the outer layer of a laminated dosage form may be printed prior to the fabrication operation, as part of the unitizing operation, or even after unitizing is completed. Dosage forms prepared by, e.g., convolute winding, can be printed while still in the continuous rod or stack. Wherein the dosage forms of the invention are sealed by the application of an overwrap, printing is preferably carried out after the overwrap is applied although it is within the scope of the invention to print on the dosage form and apply a clear overwrap thereafter. The printing of solid unit dosage forms prior to completion of compounding thereof as is comtemplated herein is a concept unique in the pharmaceutical industry.

The selection of a printing method is dependent on a variety of factors the most important of which is the physical nature of the substrate to be printed. The selection of an appropriate method is likewise relative, to a degree, to the point in the overall manufacturing operation where printing is carried out, i.e., whether the web would be printed prior to fabrication, the finished dosage forms would be printed or printing would be carried out at some intermediate point, perhaps in combination with other operations such as, for example, unitizing. The printing method and apparatus inherent thereto can be selected from the following: offset and direct letterpress; offset gravure; lithograph; electrostatic powder gravure; electrostatic screen stencil; ink jet and the like. Of these, offset gravure is the method of choice although other methods may be utilized in particular instances and new methods of printing as come to hand and are adaptable to the technology described herein are considered to be within the scope of the invention.

It will be readily apparent from the foregoing discussion of finishing and printing operations that there are a number of ways in which the color of the novel dosage forms of the present invention can be varied both in hue and intensity. First, the web composition itself can contain a color which can build in intensity as layers of web are joined during the various fabrication operations. The color may also be imparted by an overwrap or sealing layer. Wherein the basket or encapsulation methods of sealing are utilized, two or more contrasting colors may be possible by the obvious expedient of varying the color of the various sections thereof. The dosage forms prepared by lamination are also amenable to variations in color simply by varying the color of the webs fed into the laminating apparatus. Other variations of these techniques will be readily apparent to those skilled in the art.

ACTIVE INGREDIENT

The novel dosage forms of the present invention are, as a practical matter, unrestricted in terms of the type of active substance for which they can serve as a vehicle. The terms "active substance", "active ingredient" and "medicament" which are considered to be synonymous in the context of the subject invention and are utilized interchangeably throughout the instant specification and claims can be defined as any substance which will produce a pharmacologic response in the body. Such substances include but are by no means intended to be restricted to the following:

The benzodiazepines such as, for example, chlordiazepoxide, diazepam, flurazepam, oxazepam, chlorozepate and the like. Additional compounds falling under the heading "benzodiazepines" are described in "Benzodiazepines" Garattini, Mussini and Randal, Raven Press 1973 the disclosure of which is not intended as a limitation on the term;

Other tranquilizing agents such as, for example, reserpine, thiopropazate and phenothiazine compounds such as perphenazine, chlorpromazine and the like;

Sedatives and hypnotics such as the phenobarbitals, methylprylon glutethimide, ethchlorvynol, methaqualone and the like;

Psychic energizers such as, for example, amitriptyline, imipramine, methylphenidate and the like;

Narcotic and non-narcotic analgesics such as codeine, levorphanol, morphine, propoxyphene, pentazocine and the like.

Analgesic - antipyretics such as, for example, aspirin, phenacetin, salicylamide and the like;

Anti-inflammatories such as, for example, hydrocortisone, dexamethazone, prednisolone, indomethacin, phenylbutazone and the like;

Antispasmodics/anticholinergics such as, for example, atropine, papaverine, propantheline, dicyclomine, clindinium and the like;

Antihistamine/antiallergenics such as, for example, diphenhydramine, chlorpheniramine, tripelennamine, brompheniramine and the like;

Decongestants such as, for example, phenylephrine, pseudoephedrine and the like;

Diuretics such as chlorothiazide, hydrochlorothiazide, flumethiazide, triamterene, spironolactone and the like;

Nutritional substances such as, for example, vitamins, essential amino acids and the like;

Anti-Parkinsonism agents such as, for example, L-DOPA alone and in combination with potentiators such as $N^1$-DL-Seryl-$N^2$-(2,3,4-trihydroxybenzyl) hydrazine;

Androgenic steroids such as, for example, methyltestosterone and fluoxymesterone;

Progestational agents such as, for example, progesterone, ethisterone, norethynodrel, norethindrone, medroxyprogesterone and the like;

Estrogens such as, for example, estrone, ethinyl estradiol, diethyl stilbestrol and the like;

Hormonal preparations such as, for example, the prostaglandins, ACTH and the like;

Antibiotic/anti-infectives such as, for example, the penicillins, cephalophorins, tetracycline, chlortetracycline, streptomycin, erythromycin, sulfonamides such as sulfisoxazole, sulfadimethoxazole and other agents such as nitrofurazone, metronidazole and the like;

Cardiovascular agents such as, for example, nitroglycerin, pentaerythritol tetranitrate, isosorbid dinitrate, digitalis preparations, e.g. digoxin and the like;

Antacids/antiflatulents such, for example, aluminum hydroxide, magnesium carbonate, simethiocone and the like;

Other therapeutic agents and/or combinations of agents such as are recognized in the medical arts as being therapeutically useful.

The active substances as utilized in the subject invention may be in the free form or in any non-toxic pharmaceutically acceptable form wherein their therapeutic activity is retained. For example, acidic substances may be present as esters or as salts with pharmaceutically acceptable inorganic bases such as for example, the sodium salt, the potassium salt and the like or organic bases such as amines or quaternary forms. Basic substances may be present as salts with organic acids such as the acetate, the tartrate and the like. Certain substances such as, for example, ampicillin may be present in a hydrated form. In general, any pharmaceutically equivalent form of a given active substance which is recognized in the pharmaceutical compounding arts for said substance is utilizable in the dosage forms of the present invention subject, of course, to the limitation of incompatibility with the web substrate. In those few instances where such incompatibilities may exist, they are readily ascertained by simple experimentation.

The amount of the active substance or combination of substances to be incorporated into the novel dosage forms of the subject invention is usually that amount recognized as being an effective therapeutic dosage for the particular medicament. In general, the amount of active ingredient present in a single dosage form should not exceed about 500 mg with a practical upper limit being about 750 mg.

DISSOLUTION

As stated herein, the novel dosage forms of the present invention possess an extremely consistent rate of release which is also controllable to meet desired specifications. Therefore, whatever pattern of release is contemplated, the dosage forms of the subject invention exhibit a consistency of rate of release within such pattern which is superior to that exhibited by conventional solid dosage forms, e.g., tablets and capsules.

Figure 7:
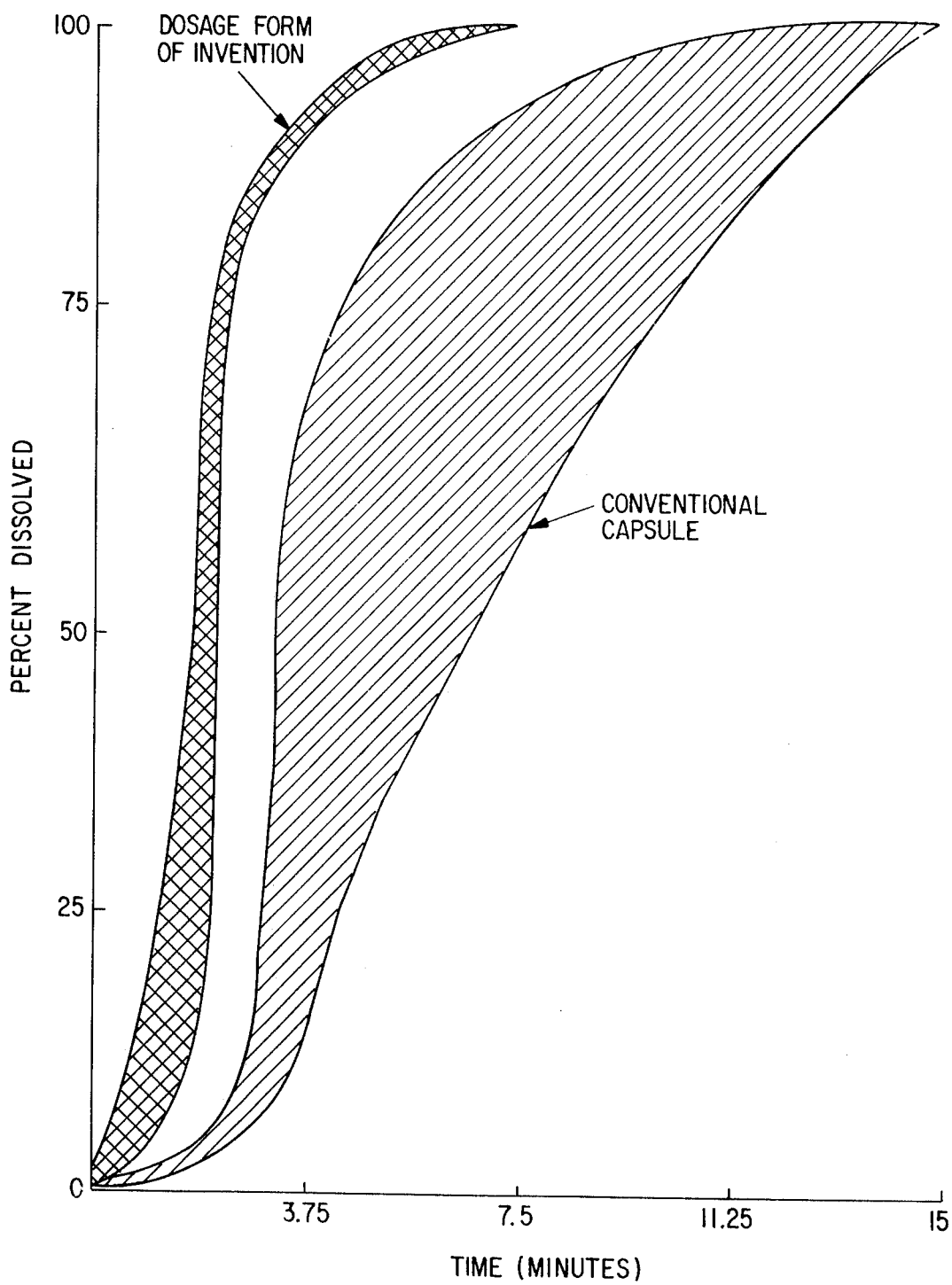
FIGS. 7 and 8 are graphic illustrations of the pattern of release of active ingredient from the dosage forms of the invention in comparison with a conventional solid dosage form, i.e., a capsule.

FIG. 7 graphically illustrates the superiority in release rate of the dosage forms of the invention in comparison with a conventional solid oral dosage form, i.e., commercial capsules. In the experiment illustrated in FIG. 7, six randomly sampled conventional capsules each containing a like amount of the same active ingredient were each placed in 100 ml. of Artificial Gastric Fluid, U.S.P. (without enzyme). The fluid was maintained with stirring at 37° C. The fluid in each of the reaction flasks was constantly flitered and circulated through flow cells in an appropriate spectrophotometer.

The absorbance of the fluids was read at one minute intervals and the percent of active ingredient dissolved calculated for each reading. In FIG. 7 the fastest and slowest dissolving sample of each group are shown and the shaded area between covers the remaining four samples. Viewing FIG. 7, two conclusions are readily reached. First, the novel dosage forms of the subject invention dissolve much more rapidly than the conventional capusles tested. Second, the variation among six samples of the dosage units of the invention was strikingly less than of the conventional capsules tested. These results clearly demonstrate the superior consistency of release which is characteristic of the dosage forms of the present invention.

Figure 8:
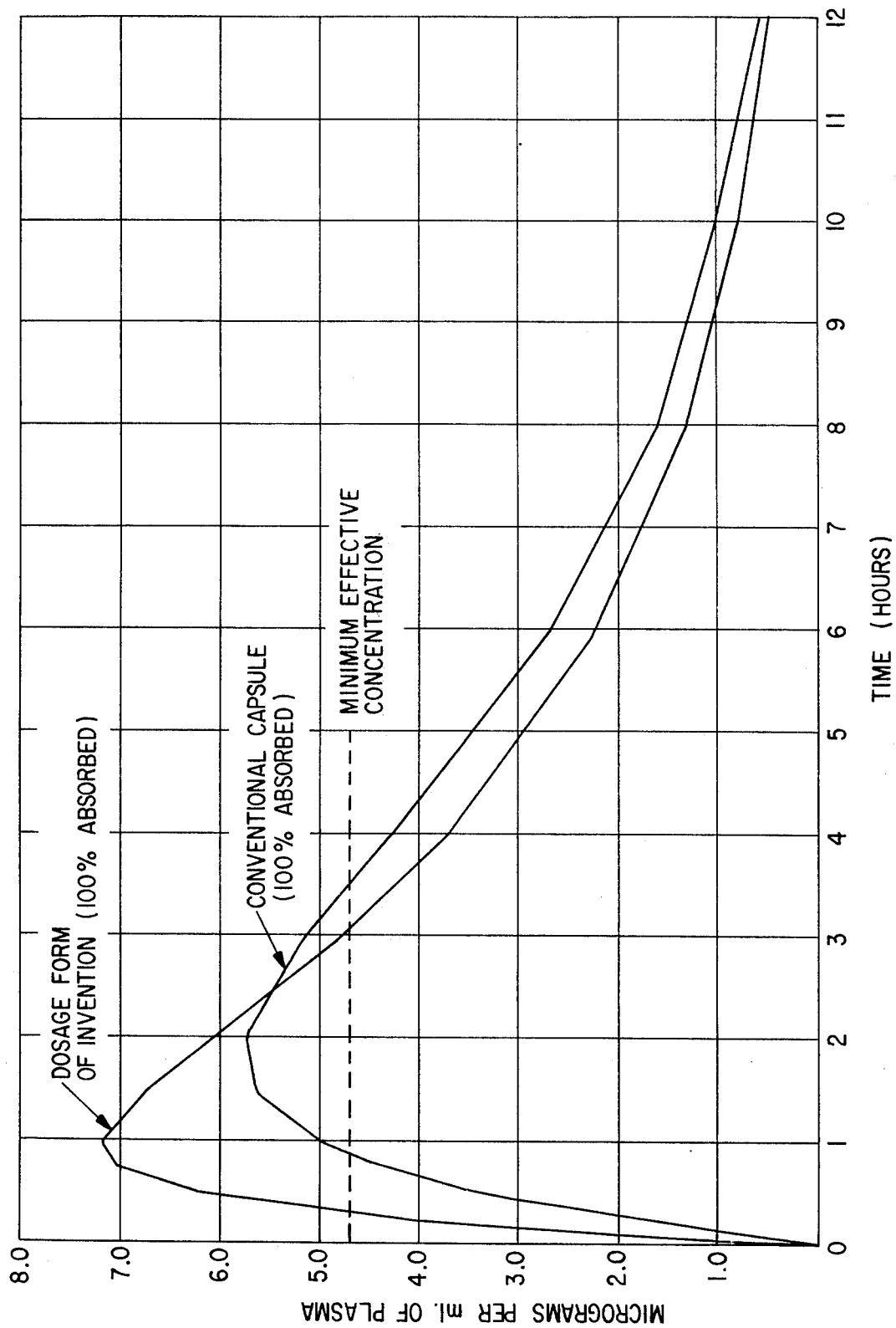

The blood level curves depicted in FIG. 8 also compare the novel dosage forms of the subject invention with commercially available capsules containing the same amount of the same active ingredient. The blood level curves are theoretically drawn based on two rates of input into a one-compartment pharmacokinetic model. The blood level curves are based on a theoretical 100% absorption of the amount of active ingredient released antiobiotics, the dosage form at a point in time and so are proportional to the dissolution rate. The difference in blood level curves is therefore a function of dissolution rates. It is clearly evident from the data illustrated FIG. 8 that the dosage forms of the subject invention not only reach effective blood levels more rapidly but attain a higher blood level of active ingredient than the conventional capsules. The ability to attain a higher blood level of active ingredient more rapidly is a distinct advantage particularly in the administration of certain types of chemotherapeutic agents, e.g., antibiotics, cardiac active agents and the like.

We claim:

1. A method of preparing solid pharmaceutical unit dosage forms comprising loading one or more medicaments to a therapeutically inert, edible web, fabricating said web into a solid geometric form of predetermined dimensions having said medicament substantially internalized, said form being divisible into a plurality of unit dosage forms, unitizing said geometric form into said plurality of unit dosage forms and sealing said unit dosage forms to completely internalize said medicament wherein said procedures include at least one non-destructive testing operation to assure uniform quality of said unit dosage forms, wherein said fabrication procedure comprises fan folding a continuous web structure comprising at least one pair of layers of web having medicament loaded to the facing surfaces thereof and subjecting said stack to pressure to densify and shape same into a continuous rod-like geometric form.

2. A method in accordance with claim 1 wherein said unit dosage forms are sealed and unitized by:
   a. placing them in perforations of cooperating shape within an endless web strap comprised of therapeutically inert, edible material;
   b. placing said web strap between two endless webs comprised of therapeutically inert, edible material and sealing said webs to said unit dosage form-containing strap thereby forming a sandwich structure completely internalizing said unit dosage forms; and
   c. transversely cutting said sandwich structure between said perforations of said perforated strap such that exposure of any part of said unit dosage forms is avoided.

3. A method in accordance with claim 2 wherein said strap has a thickness equal to or greater than $x$ and not greater than $y$ wherein $x$ is approximately ½ of the thickness of said unit dosage forms and $y$ is approximately the thickness of said unit dosage forms.

4. A method in accordance with claim 1 wherein said unit dosage forms are sealed and unitized by:
   a. placing them in perforations of cooperating shape within an endless web strap comprised of therapeutically inert, edible material, which endless perforated strap is secured initially to a first endless unperforated web comprised of therapeutically inert, edible material of comparable dimensions to said perforated web strap so as to form said perforations into bottomed receptacles for receiving said unit dosage forms;
   b. covering the open portion of said receptacles with a portion of a second endless unperforated web comprised of therapeutically inert, edible material;
   c. sealing said second web to said receptacles thereby completely internalizing said unit dosage forms; and
   d. transversely cutting said sealed strap between said perforations such that exposure of any part of said unit dosage forms is avoided.

* * * * *